US008715754B2

(12) United States Patent
Asolkar et al.

(10) Patent No.: US 8,715,754 B2
(45) Date of Patent: May 6, 2014

(54) ***CHROMOBACTERIUM* BIOACTIVE COMPOSITIONS AND METABOLITES**

(75) Inventors: Ratnakar Asolkar, Davis, CA (US); Huazhang Huang, Woodland, CA (US); Marja Koivunen, Davis, CA (US); Pamela Marrone, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 133 days.

(21) Appl. No.: 13/280,311

(22) Filed: Oct. 24, 2011

(65) Prior Publication Data

US 2012/0100236 A1  Apr. 26, 2012

Related U.S. Application Data

(60) Provisional application No. 61/406,569, filed on Oct. 25, 2010.

(51) Int. Cl.
*A61K 35/00* (2006.01)
*A01N 63/00* (2006.01)
*A61K 35/66* (2006.01)
*A61K 35/74* (2006.01)

(52) U.S. Cl.
CPC .............. *A61K 35/66* (2013.01); *A61K 35/74* (2013.01); *A61K 2236/11* (2013.01); *A61K 2236/30* (2013.01)
USPC ........................................ 424/780; 424/93.4

(58) Field of Classification Search
None
See application file for complete search history.

(56) References Cited

U.S. PATENT DOCUMENTS

| | | | |
|---|---|---|---|
| 5,047,424 | A | 9/1991 | Puritch |
| 6,077,860 | A | 6/2000 | Meunier |
| 7,244,607 | B2 | 7/2007 | Martin |
| 2003/0068304 | A1 | 4/2003 | Mattingly et al. |
| 2007/0172463 | A1* | 7/2007 | Martin et al. ............... 424/93.4 |
| 2009/0111759 | A1 | 4/2009 | Pedersen |

FOREIGN PATENT DOCUMENTS

| | | | |
|---|---|---|---|
| KR | 2007088150 A | * | 8/2007 |
| WO | 91/00012 | | 1/1991 |
| WO | 01/74161 | | 10/2001 |
| WO | WO2011110932 A | * | 11/2011 |
| WO | 2013/062977 | | 5/2013 |

OTHER PUBLICATIONS

Sanchez et al. (2006) ChemBioChem 7, 1231-1240.*
Duran et al. (2012) Med. Chem. Res. 21: 1524-1532.*
Duran et al. (2007) Biotechnol. Appl. Biochem. 48, 127-133.*
Young et al. "*Chromobacterium aquaticum* sp. nov., isolated from spring water samples" Int. J. Syst. Evol. Microbiol. 58: 877-880. 2008.
Zeck. "A Rating Scheme for Field Evaluation of Root-Knot Nematode Infestations" Pflanzenschutznachrichten Bayer 24,1: 141-144. 1971.
Asolkar et al. "Daryamides A-C, Weakly Cytotoxic Polyketides from a Marine-Derived Actinomycete of the Genus *Streptomyces* strain CNQ-085" J. Nat. Prod. 69:1756-1759. 2006.
Aspelin et al. "Pesticides Industry Sales and Usage, 1996 and 1997" U. S. E. P. Agency. Publication 733—R-99-001. 1999.
Arena et al. "The mechanism of action of avermectins in *Caenorhabditis elegans*—correlation between activation of glutamate-sensitive chloride current, membrane binding and biological activity" Journal of Parasitology 81: 286-294. 1995.
Bakhetia et al. "RNA Interference of Dual Oxidase in the Plant Nematode *Meloidogyne incognita*" Molecular Plant-Microbe Interactions 18: 1099-1106. 2005.
Balibar et al. "In Vitro Biosynthesis of Violacein from L-Tryptophan by the Enzymes VioA-E from *Chromobacterium violaceum*" Biochemistry 45: 15444-15457. 2006.
Chalvet-Monfray et al. "Synergy Between Deltamethrin and Prochloraz in Bees: Modeling Approach" Environmental Toxicology and Chemistry 15(4): 525-534. 1996.
Chitwood. "Phytochemical Based Strategies for Nematode Control" Annual Review of Phytopathology 40: 221-249. 2002.
Chitwood. "Nematicides" Encyclopedia of Agrochemicals, vol. 3. J. R. Plimmer. New York, John Wiley & Sons. 3: 1104-1115. 2003.
Colby. "Calculating Synergistic and Antagonistic Responses of Herbicide Combinations" Weeds 15(1): 20-22. 1967.
Cronin et al. "Inhibition of egg hatch of the potato cyst nematode *Globodera rostochiensis* by chitinase-producing bacteria" European Journal of Plant Pathology 57: 993-999. 1997.
Dong et al. "Microbial control of plant-parasitic nematodes: a five-party interaction" Plant Soil 288: 31-45. 2006.
Durán et al. "Minireview. Violacein: properties and biological activities" Biotechnol. Appl. Biochem. 48: 127-133. 2007.
Durán et al. "*Chromobacterium violaceum*: A Review of Pharmacological and Industrial Perspectives." Cult. Rev. Microbiol. 27: 201-222. 2001.
Farenhorst et al. "Synergy in Efficacy of Fungal Entomopathogens and Permethrin against West African Insecticide-Resistant *Anopheles gambiae* Mosquitoes" PLoS ONE 5(8): e12081. 2010.
Faske et al. "Sensitivity of *Meloidogyne incognita* and *Rotylenchulus reniformis* to abamectin" Journal of Nematology 38: 240-244. 2006.
Guerena. "Nematode: Alternative Controls" from www.attra.ncat.org/attra-pub/pdf/nematode.pdf. 2006.

(Continued)

*Primary Examiner* — Chris R Tate
*Assistant Examiner* — Russell Fiebig
(74) *Attorney, Agent, or Firm* — Yuko Soneoka

(57) ABSTRACT

Provided are bioactive compounds and metabolites derived from *Chromobacterium* species culture responsible for controlling pests, compositions containing these compounds, methods for obtaining these compounds and methods of using these compounds and compositions for controlling pests.

20 Claims, 9 Drawing Sheets

(56) References Cited

OTHER PUBLICATIONS

Hallman et al. "Toxicity of fungal endophyte secondary metabolites to plant-parasitic nematodes and soil-borne pathogens" Journal of Plant Pathology 102: 155-162. 1996.
Hasky-Gunther et al. "Resistance against potato cyst nematode *Globodera pallida* systemically induced by the rhizobacteria *Agrobacterium radiobacter*(G12) and *Bacillus spaericus* (B43)" Fundamentals of Applied Nematology 21: 511-517. 1998.
Hoshino et al. "Biosynthesis of Violacein: Origins of the Hydrogen, Nitrogen and Oxygen Atoms in the 2-Pyrrolidone Nucleus" Agric. Biol. Chem. 51: 2733-2741. 1987.
Hummelbrunner et al. "Acute, Sublethal, Antifeedant, and Synergistic Effects of Monoterpenoid Essential Oil Compounds on the Tobacco Cutworm, *Spodoptera litura* (Lep., Noctuidae)" J. Agric. Food Chem. 49(2): 715-720. 2001.
Hungria et al. "Genetic characterization of *Chromobacterium* isolates from black water environments in the Brazilian Amazon" Lett. Appl. Microbiol. 41: 17-23. 2005.
International Search Report and Written Opinion Issued in Counterpart PCT Appln. No. PCT/US2011/057541, Dated: Jun. 26, 2012.
Jaffee et al. "Susceptibility of root-knot and cyst nematodes to the nematode-trapping fungi *Monocrosporium ellipsosporum* and *M. cionopagum*" Soil Biology and Biochemistry 27: 1983-1090. 1995.
Kämpfer et al. "*Chromobacterium piscinae* sp. nov. and *Chromobacterium pseudoviolaceum* sp. nov., from environmental samples" Int. J. Syst. Evol. Microbiol. 59: 2486-2490. 2009.
Kerry. "Exploitation of the nematophagous fungal *Verticillium chlamydosporium* Goddard for the biological control of root-knot nematodes (*Meloidogyne* spp.) Fungi as biocontrol agents: Progress, problems and potential" T. M. Butt, C. Jackson and N. Magan. New York, CAB International: 155-168. 2001.
Kirkegaard et al. "Biofumigation potential of brassicas" Plant and Soil 201: 71-89. 1998.
Koenning et al. "Survey of Crop Losses in Response to Phytoparasitic Nematodes in the United States for 1994" Journal of Nematology 31: 587-618. 1999.
Kokalis-Burrelle et al. "Allelochemicals as biopesticides for management of plant-parasitic nematodes. Alleolochemicals: Biological Control of Plant Pathogens and Diseases" Inderjit and K. G. Mukerji. Netherlands, Springer: 15-29. 2006.
Krieg et al. "*Bacillus thuringiensis* var. *tenebrionis*: Ein neuer, gegenuber Larven von Coleopteren wirksamer Pathotyp" Z. Angew. Entomol. 96: 500-508. 1983. (English Abstract).
Martin et al. "*Chromobacterium substugae* sp. nov., a betaproteobacterium toxic to Colorado potato beetle and other insect pests" Int. J. Syst. Evol. Microbiol. 57: 993-999. 2007a.
Martin et al. "Toxicity of *Chromobacterium substugae* to Southern Green Stink Bug (Heteroptera:Pentatomidae) and Corn Rootworm (Coleoptera:Chrysomelidae)" J. Econ. Entomol. 100: 680-684. 2007b.
Martin. "A freeze-dried diet to test pathogens of Colorado potato beetle" Biological Control 29(1): 109-114. 2004.
McClean et al. "Quorum sensing and *Chromobacterium violaceum*: exploitation of violacein production and inhibition for the detection of N-acyl homoserine lactones" Microbiology 143: 3703-3711. 1997.
Meyer et al. "Combinations of Biocontrol Agents for Management of Plant-Parasitic Nematode and Soilborne Plant-Pathogenic Fungi" Journal of Nematology 34: 1-8. 2002.
Oka et al. "Nematicidal Activity of Essential Oils and Their Components Against Root-Knot Nematode" Phytopathology 90:710-715. 2000.
Oostendorp et al. "In-vitro interrelationships between rhizosphere bacteria and *Heterodera schachtii*" Reviews in Nematology 13: 269-274. 1990.
Quarles. 2005 Directory of least toxic pest control products The IPM Practitioner 26: 17. 2005.
Roubtsova et al. "Effect of Broccoli (*Brassica oleracea*) Tissue, Incorporated at Different Depths in a Soil Column, on *Meloidogyne incognita*" Journal of Nematology 39: 111-117. 2007.
Ryan et al. "Divergent pathways in the biosynthesis of bisindole natural products" Chem. Biol. 16: 351-364. 2009.
Sasser et al. "A World Perspective on Nematology: The Role of the Society" In J.A. Veech and D.W. Dickson (Eds.), Vistas on Nematology (pp. 7-14). Society of Nematologists, Hyatsville. 1987.
Saxena et al. "Bacterial biocontrol agents and their role in plant disease management. Biocontrol potential and its exploitation in sustainable agriculture: crop diseases, weeds and nematodes" R. R. Upadhaya, K. G. Mekerji and B. P. Chamola. New York, Kluwer Academy Plenum. 2000.
Shapiro-Ilan et al. "Effects of Combining Microbial and Chemical Insecticides on Mortality of the Pecan Weevil (Coleoptera: Curculionidae)" J Econ Entomol 104(1): 14-20. 2011.
Siddiqui et al. "Biological control of plant parasitic nematodes by fungi: a review" Bioresource Technology 58: 229-239. 1996.
Siddiqui et al. "Role of bacteria in the management of plant parasitic nematodes: a review" Bioresource Technology 69: 167-179. 1999.
Siddiqui et al. "Nematicides" The IPM practitioner 9-11. 2001.
Sikora et al. "Biological control of plant-parasitic nematodes with plant-health promoting rhizobacteria" In: Lumsden R.D., Vaughn J.L (eds): Pest Management: Biologically Based Technologies. Proceedings of Beltsville Symposium XVIII, Washington. American Chemical Society: 166-172. 1993.
Terefe et al. "Effect of a formulation of *Bacillus firmus* on root-knot nematode *Meloidogyne incognita* infestation and the growth of tomato plants in the greenhouse and nursery" Journal of Invertebrate Pathology 100: 94-99. 2009.
Thompson et al. "Spinosad—a case study: an example from a natural products discovery programme" Pest Manag Sci 56: 696-702. 2000.
Whitehead. "Plant nematode control" Wallingford, UK, CAB International. 1998.
Wirth et al. "Synergy between Toxins of *Bacillus thuringiensis* subsp. *israelensis* and *Bacillus sphaericus*" J. Med. Entomol. 41: 935-941. 2004.

\* cited by examiner

Chromamide A (1)

Violacein (2)

Deoxyviolacein (3)

CHROMOBACTERIUM BIOACTIVE COMPOSITIONS AND METABOLITES

TECHNICAL FIELD

Disclosed herein are bioactive compositions and metabolites derived from *Chromobacterium* and particularly *Chromobacterium substugae* culture responsible for controlling pests as well as their methods of use for controlling pests.

BACKGROUND ART

Natural products are substances produced by microbes, plants, and other organisms. Microbial natural products offer an abundant source of chemical diversity, and there is a long history of utilizing natural products for pharmaceutical purposes. Despite the emphasis on natural products for human therapeutics, where more than 50% are derived from natural products, only 11% of pesticides are derived from natural sources. Nevertheless, natural product pesticides have a potential to play an important role in controlling pests in both conventional and organic farms. Secondary metabolites produced by microbes (bacteria, actinomycetes and fungi) provide novel chemical compounds which can be used either alone or in combination with known compounds to effectively control insect pests and to reduce the risk for resistance development. There are several well-known examples of microbial natural products that are successful as agricultural insecticides (Thompson et al., 2000; Arena et al., 1995; Krieg et al. 1983).

The development of a microbial pesticide starts with the isolation of a microbe in a pure culture. It then proceeds with efficacy and spectrum screening using in vitro, in vivo or pilot scale trials in a greenhouse and in the field. At the same time, active compounds produced by the microbe are isolated and identified. For the commercialization of a microbial pesticide, the microbe has to be economically produced by fermentation at an industrial scale and formulated with biocompatible and approved additives to increase efficacy and to maximize the ease of application as well as storage stability under field conditions.

As farmers look to expand their insecticide arsenal and as new microbial products are placed on the market, there is a potential for a variety of interactions to occur between new and old insecticides. Combinations of 2 or more insecticides applied to a single crop simultaneously or sequentially have often been used. To address these concerns, scientists have examined the interaction of oils, fungi, and chemical pesticides against pest and beneficial insects using topical and feeding methods (see, for example, Chalvet-Monfray, Sabatier et al. 1996; Meunier, Carubel et al. 1999; Hummelbrunner and Isman 2001; Wirth, Jiannino et al. 2004; Farenhorst, Knols et al. 2010; Shapiro-Ilan, Cottrell et al. 2011); however, not all interactions have yet been studied.

Chromobacterium

The Beta-Proteobacterium strain, *Chromobacterium subtsugae*, exhibits insecticidal activity against a wide variety of insects (Martin, Blackburn et al. 2004; Martin 2004; Martin, Gundersen-Rindal et al. 2007; Martin, Hirose et al. 2007; Martin, Shropshire et al. 2007). The mode of action appears to be a combination of antifeedant and toxin activity, with feeding inhibition observed at sublethal doses (Martin, Gundersen-Rindal et al. 2007). In particular, it has been found that *Chromobacterium substugae* are effective against adult Colorado Potato Beetle (*Leptinotarse decemlineata*), adult Western Corn Rootworm (*Diabrotica virgifera*), adult and larval Southern Corn Rootworm (*Diabrotica undecimpunctata*), larval Small hive beetle (*Aethina tumida*), larval Diamondback Moths (*Plutella xyllostella*), adult and larval Sweet Potato Whitefly (*Bernisia tabaci*) and adult Southern Green Stinkbug (*Nezara viridula*). Since the finding of *C. substugae* by Martin and her coworkers, at least three new species of Chromobacteria have been isolated, and characterized; Young et al. (2008) isolated a novel *Chromobacterium* species, *C. aquaticum*, from spring water samples in Taiwan, and Kampfer et al. (2009) isolated two species, *C. piscinae* and *C. pseudoviolaceum*, from environmental samples collected in Malaysia.

Secondary Metabolites of the Genus *Chromobacterium*

Of all known species of Chromobacteria, *Chromobacterium violaceum* is studied the most, and published information on secondary metabolites produced by Chromobacteria is based on studies on *Chromobacterium violaceum* only. Durán and Menck (2001) have published a comprehensive review of the pharmacological and industrial perspectives of *Chromobacterium violaceum*, a Gram-negative saprophyte from soil and water. It is normally considered nonpathogenic to humans, but as an opportunistic pathogen, it has occasionally been the causative agent for septicemia and fatal infections in humans and animals. *Chromobacterium violaceum* is known to produce a purple pigment, violacein, which is a bisindole molecule generated by a fusion of two L-tryptophan molecules in the presence of oxygen (Hoshino et al., 1987; Ryan and Drennan; 2009). Violacein biosynthesis is regulated by quorum-sensing, a common mechanism regulating various other secondary metabolism pathways in Gram-negative bacteria (McClean et al., 1997).

Other known metabolites of *Chromobacterium violaceum* summarized by Durán and Menck (2001) include hydrogen cyanide, ferrioxamine E, B-lactamic glycopeptides SQ28, 504 and SQ28,546, antibiotics such as aerocyanidin, aerocavin, 3,6-dihydroxy-indoxazene, and monobactam SB-26.180, and an antitumoral depsipeptide FR901228. According to the review article by Durán and Menck (2001), *Chromobacterium violaceum* also produces unusual sugar compounds such as extracellular polysaccharides and lipopolysaccharides.

Nematodes and Nematocides

Nematodes are non-segmented, bilaterally symmetric, worm-like invertebrates that possess a body cavity and complete digestive system but lack respiratory and circulatory systems. Their body wall is composed of a multilayer cuticle, a hypodermis with four longitudinal cords, and internal musculature (Chitwood, 2003). Their body contents are mostly occupied by digestive and reproductive systems. Most nematodes are free-living but a smaller number of species are ubiquitous parasites of animals or plants.

Root-knot nematodes (*Meloidogyne* spp.) parasitize a wide range of annual and perennial crops, impacting both quality and quantity of marketable yields. Nematodes in this genus are considered the most economically important plant parasitic nematodes (Whitehead, 1998). Annual crop losses caused by plant-parasitic nematodes have been estimated to exceed US $100 billion (Koenning et al. 1999), with more than half caused by the genus *Meloidogyne*. The inoculum in this strain comes from eggs that under favorable conditions hatch to release infective second stage larvae (J2s), which migrate in the soil towards a host plant root. Infection occurs through root tip penetration, after which the larvae move to vascular tissue where the nematode becomes sedentary, feeding directly from plant cells. The plant responds by producing giant cells that form galls (root knots). Throughout the reproductive life, females remain imbedded in the plant tissue, and only the egg masses protrude from the root.

The most efficient means for controlling root-knot nematodes is via nematicides that inhibit either egg hatching, juvenile mobility and/or plant infectivity. The development of chemical control for plant-parasitic nematodes is challenging because of both environmental and physiological reasons: 1. Most phytoparasitic nematodes live in a confined area in soil near the roots and hence, delivery of a chemical nematicide is difficult. 2. The outer surface of nematodes is a poor biochemical target, and is impermeable to many organic molecules (Chitwood, 2003). Moreover, delivery of toxic compounds by an oral route is nearly impossible because most plant parasitic nematode species ingest material only after they have penetrated and infected plant roots. Therefore, nematicides have tended to be broad-spectrum toxins with high volatility or with other chemical and physical properties promoting their mobility in soil.

During the past decade, halogenated hydrocarbons (e.g. ethylene dibromide, methyl bromide) have been the most heavily used nematicides around the world. Due to their high human toxicity and detrimental effects on stratospheric ozone layer these compounds were banned in the Montreal Protocol but the use of methyl bromide for nematode and plant pathogen control was extended in the US due to lack of substitution products. Along with organophosphates, carbamates are the most effective non-fumigant nematicides. Unfortunately, most carbamates such as aldicarb and oxamyl are also highly toxic. As of August 2010, the manufacturer of aldicarb, Bayer, has agreed to cancel all product registrations on potatoes and citrus in the US, and aldicarb will be completely phased out by the end of August, 2018. Recently, abamectin—a mixture of two avermectins produced by a soil actinomycete, *Streptomyces avermitilis*—has been registered for nematicidal use (Faske and Starr, 2006). Syngenta markets this active ingredient as a seed treatment for cotton and vegetables under the trade name Avicta®.

Several microbial plant/nematode pathogens have been reported to be active against plant parasitic nematodes (Guerena, 2006). These biological control agents include the bacteria *Bacillus thuringiensis, Burkholderia cepacia, Pasteuria penetrans* and *P. usgae*. Pasteuria Biosciences has launched *P. usgae* against sting nematodes on turf in the southeastern US. Nematicidal fungi include *Trichoderma harzianum, Hirsutella rhossiliensis, H. minnesotensis, Verticillium chlamydosporum, Arthrobotrys dactyloides*, and *Paecilomyces lilanicus* (marketed as BioAct® and Melcon® by Prophyta). Another fungus, *Myrothecium verrucaria* is available in a commercial formulation, DiTera®, by Valent Biosciences. This is a killed fungus; hence the activity is due to nematicidal compounds. Other commercial bionematicides include Deny® and Blue Circle® (*B. cepacia*), Activate® (*Bacillus chitinosporus*) (Quarles, 2005) and an Israeli product BioNem® (*Bacillus firmus*) (now marketed by Bayer as a seed treatment Votivo®) (Terefe et al. 2009). It has been hypothesized that the detrimental effect of microbial isolates on nematode egg hatching, juvenile mobility and infectivity can be attributed to toxins produced by these organisms (Hallman and Sikora, 1996; Marrone et al, 1998; Siddiqui and Mahmood, 1999; Saxena et al., 2000; Meyer and Roberts, 2002), ability to parasitize or even trap nematodes (Siddiqui and Mahmood, 1996; Kerry, 2001; Jaffee and Muldoon, 1995), induction of systemic resistance (Hasky-Gunther et al. 1998), changing nematode behavior (Sikora and Hoffman-Hergarter, 1993) or interfering with plant recognition (Oostendorp and Sikora, 1990)

Botanical nematicides, such as plant extracts and essential oils, can be used to control nematodes (Kokalis-Burrelle and Rodriguez-Kabana, 2006). Chitwood has summarized the options of using plant-derived compounds for nematode control in his recent review article (Chitwood, 2002). Siddiqui and Alam (2001) demonstrated that potting soil amended with plant parts from the neem tree (*Azadirachta indica*) and Chinaberry tree (*Melia azadirah*) inhibited root-knot nematode development of tomatoes. However, no neem products are currently registered in the US for use against nematodes. A new botanical product from Chile (Nema-Q®) based on a *Quillaja saponaria* tree extract containing saponins (bidesmosidic derivatives of quillajic acid substituted with a trisaccharide at C-3 and an oligosaccharide in C-28) has been recently registered as a an organic nematicide through US EPA and listed for organic farming by the Organic Materials Review Institute (OMRI). It is marketed by Monterey AgResources.

Crop rotation to a non-host crop is often adequate by itself to prevent nematode populations from reaching economically damaging levels (Guerena 2006). Allelochemicals are plant-produced compounds that affect the behavior of organisms in the plant's environment. Examples of nematocidal allelochemicals include polythienyls, glucisonolates, alkaloids, lipids, terpenoids, steroids, triterpenoids and phenolics (Kokalis-Burrelle and Rodriguez-Kabana, 2006; Chitwood, 2002). When grown as cover crops, bioactive compounds from allelopathic plants are exuded during the growing period and/or released to the soil during biomass decomposition. *Brassica* crops can be used for biofumigation—a pest management strategy based on the release of biocidal volatiles during decomposition of soil-incorporated tissue (Kirkegaard and Sarwar, 1998). However, studies of Roubtsova et al (2007) on the effect of decaying broccoli tissue on *M. incognita* numbers indicated that for proper control, thorough mixing of plant tissue with the complete nematode-infected soil volume was necessary.

The future of nematode control in agricultural soils relies on two factors: development of nematode resistant crops and the discovery and development of new, broad-spectrum, less toxic nematicides. The cost of research, development and registration of a new chemical nematicides is extremely high (>$200 million), which limits their development. Of the 497 new active ingredients registered for use as a pesticide from 1967 to 1997, only seven were registered as nematicides (Aspelin and Grube, 1999). Besides conventional chemical methods, RNA interference (RNAi) has been proposed as a method for controlling nematodes. Use of gene silencing via RNAi was first demonstrated on *Caenorhabditis elegans* and quite recently also for plant parasitic nematodes such as *Meloidogyne* spp. (Bakhetia et al. 2005). The search for new microbial strains to use as sources for biological nematicides is an important goal in order to reduce the significant economic damage caused by plant-parasitic nematodes as well as to reduce the use of toxic compounds currently registered for nematode control.

According to Sasser and Freckman (1987), crop losses by nematodes range from 8 to 20% on major crops around the world. Plant parasitic nematodes can cause considerable crop damage with annual losses estimated at $87 billion worldwide (Dong and Zhang, 2006). Nematode resistant crop varieties and chemical nematicides are currently the main options for nematode control. Fumigants such as methyl bromide are very effective in controlling both soil-borne plant diseases and nematodes but due to the high mammalian toxicity, ozone depleting effects and other residual effects, the use of methyl bromide has already been banned in various countries and its complete withdrawal from the market is planned by international agreement (Oka et al., 2000). Chemical alternatives such as methyl iodide, 1,3-Dichloropropene, and cholorpicrin also have issues with mammalian and environmental safety. Chemical non-fumigant nematicides are being phased out and banned. Most recently, the US-EPA announced that aldicarb was being phased out.

BRIEF SUMMARY

Provided herein are novel uses and combinations and, in particular, compositions comprising a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607.

Thus provided herein is a method for modulating nematode infestation in a plant comprising applying to a plant, and/or seeds thereof and/or substrate used for growing said plant an amount of a supernatant, filtrate and/or extract and/or one or more metabolites from said supernatant, filtrate and/or extract of a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 and optionally another nematocidal substance in an amount effective to modulate said nematode infestation.

Also provided herein is a pesticidal combination synergistic to at least one pest comprising as active components: (a) a supernatant, filtrate and/or extract of a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 and/or one or more metabolite(s) from said supernatant, filtrate and/or extract of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 and (b) another pesticidal substance, wherein (a) and (b) are present in synergistic amounts. The pest, in a particular embodiment, may be an insect pest, but may also include, but is not limited to, a nematode, plant fungus, plant virus and plant bacteria and weeds. Further, the combination may be a composition. The pesticidal substance may be (a) derived from a microorganism; (b) a natural product and/or (c) a chemical pesticide and in particular a chemical nematocide.

In particular, the combination may comprise a supernatant, filtrate and/or extract of a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 and a pesticidal substance derived from a microorganism including but not limited to *Bacillus* sp. (e.g., *Bacillus thuringiensis* or *Bacillus thuringiensis kurstaki*) and spinosad. Althernatively, the combination may comprise a supernatant, filtrate and/or extract of a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 and a pesticidal substance derived from a natural product such as pyrethrum. Althernatively, the combination may comprise a supernatant, filtrate and/or extract of a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 and a pesticidal substance which is a chemical pesticide, particularly, an insecticide, where the insecticide includes but is not limited to pyrethrins, spirotetramet and anthranilicdiamide.

In a related aspect, provided herein is a method for synergistically modulating infestation of at least one pest or pest species in a plant comprising applying to a plant and/or seeds thereof and/or substrate for growing said plant the combinations set forth above with an amount of the combination effective to modulate infestation of said pest or pest species. Also provided herein are isolated compounds obtainable or derived from a strain of *Chromobacterium* species, more particularly, *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 or alternatively, organisms capable of producing these compounds that can be used to control various pests, and particularly, nematocidal pests.

In one embodiment, the compound may be a compound that (a) has pesticidal activity; (b) has a molecular weight of about 840-900 as determined by Liquid Chromatography/Mass Spectroscopy (LC/MS) and (c) has an High Pressure Liquid Chromatography (HPLC) retention time of about 7-12 minutes on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm and (d) is optionally obtainable from a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607. The compound in one embodiment may be a peptide.

In a particular embodiment, the compound has 43 carbons, seven methyl, ten methylene carbons, twelve methines, 6 olefinic methines, and eight quaternary carbons as determined by $^{13}C$ NMR.

In one specific embodiment, the compound "A": (a) is obtainable from a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607; (b) is toxic to a pest; (c) has a molecular weight of about 840-890 and more particularly, 860 as determined by Liquid Chromatography/Mass Spectroscopy (LC/MS); (d) has $^1H$ NMR values of δ 8.89, 8.44, 8.24, 8.23, 7.96, 7.63, 6.66, 5.42, 5.36, 5.31, 5.10, 4.13, 4.07, 4.05, 3.96, 3.95, 3.88, 3.77, 3.73, 3.51, 3.44, 3.17, 2.40, 2.27, 2.11, 2.08, 2.03, 2.01, 1.97, 1.95, 1.90, 1.81, 1.68, 1.63, 1.57, 1.53, 1.48, 1.43, 1.35, 1.24, 1.07, 1.02, 0.96, 0.89, 0.88, 0.87, 0.80 and has $^{13}C$ NMR values of δ 173.62, 172.92, 172.25, 172.17, 171.66, 171.28, 170.45, 132.13, 130.04, 129.98, 129.69, 129.69, 125.48, 98.05, 70.11, 69.75, 68.30, 68.25, 64.34, 60.94, 54.54, 52.82, 49.72, 48.57, 45.68, 40.38, 39.90, 38.18, 36.60, 31.98, 31.62, 31.58, 29.53, 28.83, 27.78, 24.41, 23.06, 22.09, 20.56, 19.31, 18.78, 17.66, 15.80 (e) has an High Pressure Liquid Chromatography (HPLC) retention time of about 7-12 minutes, more specifically about 9 minutes and even more specifically about 9.08 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm. In particular, the $^{13}C$ NMR spectrum reveals signals for 43 carbons, for seven methyl, ten methylene carbons, twelve methines, 6 olefinic methines, eight quaternary carbons and/or the $^1H$ NMR spectrum displays characteristics of a typical peptide, illustrating five amide NH signals [$\delta_H$: 8.89, 8.44, 8.23, 8.22, 7.96], one amine $NH_2$ signal [$\delta_H$: 7.64, 6.65], six α-amino protons [$\delta_H$: 4.07, 4.06, 3.96, 3.95, 3.88, 3.72] and in the $^{13}C$ NMR spectrum, six/seven amide or ester resonances [$\delta_C$: 173.62, 172.92, 172.25, 1.72.17, 171.66, 171.28, 170.45].

In another specific embodiment, the compound "B" has the following characteristics: (a) is obtainable from a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607; (b) is toxic to a pest; (c) has a molecular weight of about 850-900 and more particularly, 874 as determined by Liquid Chromatography/Mass Spectroscopy (LC/MS); (d) has an High Pressure Liquid Chromatography (HPLC) retention time of about 7-12 minutes, more specifically about 9 minutes and even more specifically about 9.54 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm.

In a more particular embodiment, provided are compounds including but not limited to:

(A) a compound having the structure ##STR001##

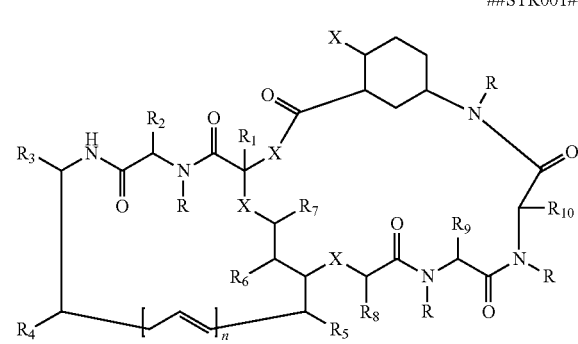

STR001## or a pesticidally acceptable salt or steriosomers thereof, wherein R is —H, lower chain alkyl containing 1, 2, 3, 4, 5, 6, 7, 8 or 9 alkyl moieties, aryl or arylalkyl moiety, substituted lower alkyl; X is O, NH, NR or S; n is 0, 1, 2, 3, 4, 5, 6, 7, 8 or 9; $R_1$, $R_2$, $R_3$, $R_4$, $R_5$, $R_6$, $R_7$, $R_8$, $R_9$, $R_{10}$, $R_{11}$ are each independently H, are the same or different and independently an amino acid side-chain moiety or an amino acid side-chain derivative, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(B) a compound having the structure ##STR001a##

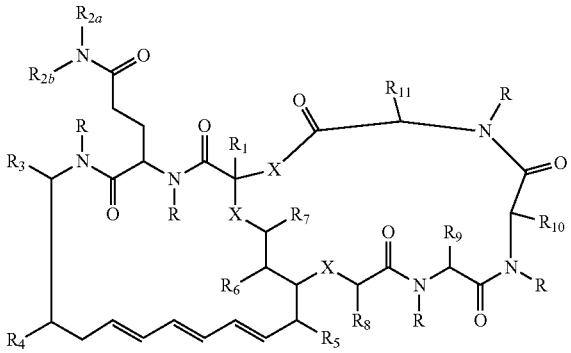

STR001a## wherein R is —H, lower chain alkyl containing 1, 2, 3, 4, 5, 6, 7, 8 or 9 alkyl moieties, aryl or arylalkyl moiety, substituted lower alkyl; X is O, NH, NR or S; R2a, R2b are independently selected from the group consisting of —H, alkyl, lower-alkyl, substituted alkyl and substituted lower-alkyl; $R_1$, $R_2$, $R_3$, $R_4$, $R_5$, $R_6$, $R_7$, $R_8$, $R_9$, $R_{10}$, $R_{11}$ are each independently H, are the same or different and independently an amino acid side-chain moiety or an amino acid side-chain derivative, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

(C) a compound having the structure ##STR001b##

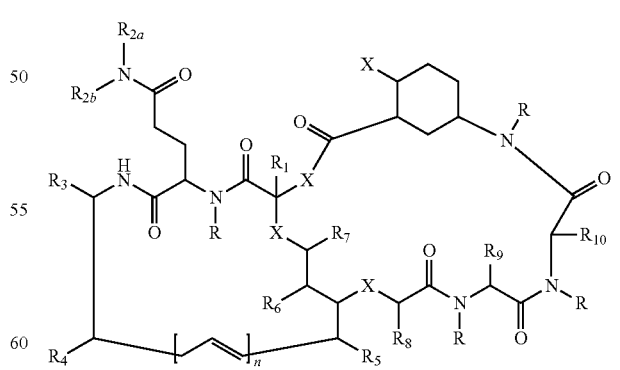

STR001b## wherein R is —H, lower chain alkyl containing 1, 2, 3, 4, 5, 6, 7, 8 or 9 alkyl moieties, aryl or aryl alkyl moiety, substituted lower alkyl; X is O, NH, NR or S; n is 0, 1, 2, 3, 4, 5, 6, 7, 8 or 9; R2a, R2b are independently selected from the group consisting of —H, alkyl, lower-alkyl, substituted alkyl and substituted lower-alkyl; $R_1$, $R_2$, $R_3$, $R_4$, $R_5$, $R_6$, $R_7$, $R_8$, $R_9$, $R_{10}$, $R_{11}$ are each independently H, are the same or different and independently an amino acid side-chain moiety or an amino acid side-chain derivative, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

(D) a compound having the structure ##STR001c##

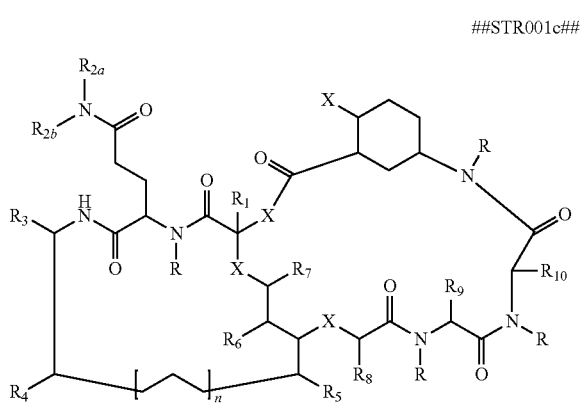

STR001c## wherein R is —H, lower chain alkyl, aryl or aryl alkyl moiety, substituted lower alkyl containing 1, 2, 3, 4, 5, 6, 7, 8 or 9 alkyl moieties; X is O, NH, NR or S; n is 0, 1, 2, 3, 4, 5, 6, 7, 8 or 9; R2a, R2b are independently selected from the group consisting of —H, alkyl, lower-alkyl, substituted alkyl and substituted lower-alkyl; $R_1$, $R_2$, $R_3$, $R_4$, $R_5$, $R_6$, $R_7$, $R_8$, $R_9$, $R_{10}$, $R_{11}$ are each independently H, are the same or different and independently an amino acid side-chain moiety or an amino acid side-chain derivative, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

In a more particular embodiment, the compound is chromamide A (1).

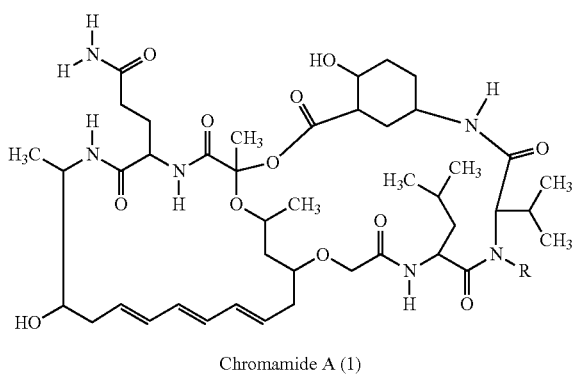

Chromamide A (1)

These compounds may be obtained by (a) culturing a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 in a culture medium or whole cell broth under conditions sufficient to produce said compound to obtain a *Chromobacterium* culture and (b) isolating said compound produced from the whole cell broth of (a). In particular, the compound in step (b) may be isolated by (i) applying the whole cell broth to at least one of an ion exchange column, a size exclusion column or a reversed phase HPLC column to obtain column fractions; (ii) assaying the column fractions for pesticidal activity and (iii) concentrating column fractions of (ii) to obtain isolated compound.

Further provided are compositions, particularly pesticidal compositions comprising said compounds as well as other compounds obtainable from a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 with pesticidal activity. These other compounds may have the following characteristics: (a) a molecular weight of about 315-360 as determined by Liquid Chromatography/Mass Spectroscopy (LC/MS); (b) an High Pressure Liquid Chromatography (HPLC) retention time of about 8-15 minutes on a reversed phase C-18 HPLC column using a water: acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm and may be obtained by (A) culturing a a strain of *Chromobacterium* sp., particularly a strain of *Chromobacterium* substugae and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607 in a culture medium under conditions sufficient to produce said compound to obtain a a strain of *Chromobacterium* sp., particularly a strain of *Chromobacterium substugae* and more particularly, a strain of *Chromobacterium substagae* sp. nov. and even more particularly a strain of *Chromobacterium* substagae sp. nov. having the identifying characteristics of NRRL B-30655 described in U.S. Pat. No. 7,244,607 culture and (B) isolating said compound produced from the whole cell broth of (A).

In a particular embodiment, one compound used in said composition set forth above, compound "C", has the following characteristics: (a) is obtainable from a strain of *Chromobacterium* sp., particularly a strain of *Chromobacterium substugae* and more particularly, a strain of *Chromobacterium substagae* sp. nov. and even more particularly a strain of *Chromobacterium substagae* sp. nov. having the identifying characteristics of NRRL B-30655 described in U.S. Pat. No. 7,244,607; (b) is toxic to pests; (c) has a molecular weight of about 325-360 and more particularly, about 343 as determined by Liquid Chromatography/Mass Spectroscopy (LC/MS); (d) has an High Pressure Liquid Chromatography (HPLC) retention time of about 8-14 minutes, more specifically about 10 minutes and even more specifically about 10.88 min on a reversed phase C-18 HPLC (Phenomenex, Luna 5µ C18(2) 100 A, 100×4.60 mm) column using a water: acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm. In a particular embodiment, compound "C" may be violacein (2), a known compound isolated earlier from *Chromobacterium violaceum.*

In another embodiment, another compound used in the composition set forth above, the compound "D", has the following characteristics: (a) is obtainable from a *Chromobacterium* species; (b) is toxic to a pest; (c) has a molecular weight of about 315-350 and more particularly, about 327 as determined by Liquid Chromatography/Mass Spectroscopy (LC/MS); (d) has an High Pressure Liquid Chromatography (HPLC) retention time of about 10-15 minutes, more specifically about 12 minutes and even more specifically about 12.69 min on a reversed phase C-18 HPLC (Phenomenex, Luna 5μ C18(2) 100 A, 100×4.60 mm) column using a water: acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm. In a particular embodiment, compound "D" may be characterized as deoxyviolacein (3), a known compound isolated earlier from *Chromobacterium violaceum.*

Said compositions may further optionally comprise a second substance, wherein said second substance is a chemical or biological pesticide and/or at least one of a carrier, diluent, surfactant or adjuvant.

Also provided is a method of using the compounds (e.g., compounds "A", "B", "C" and "D") and compositions set forth above to modulate pest infestation, particularly nematocidal pests in a plant comprising applying to the plant an amount of the compound or compositions and optionally a second chemical or biological pesticide effective to modulate said pest infestation. Further provided is the use of the compounds set forth above for formulating a composition for modulating pest infestation in a plant.

Figure 1:
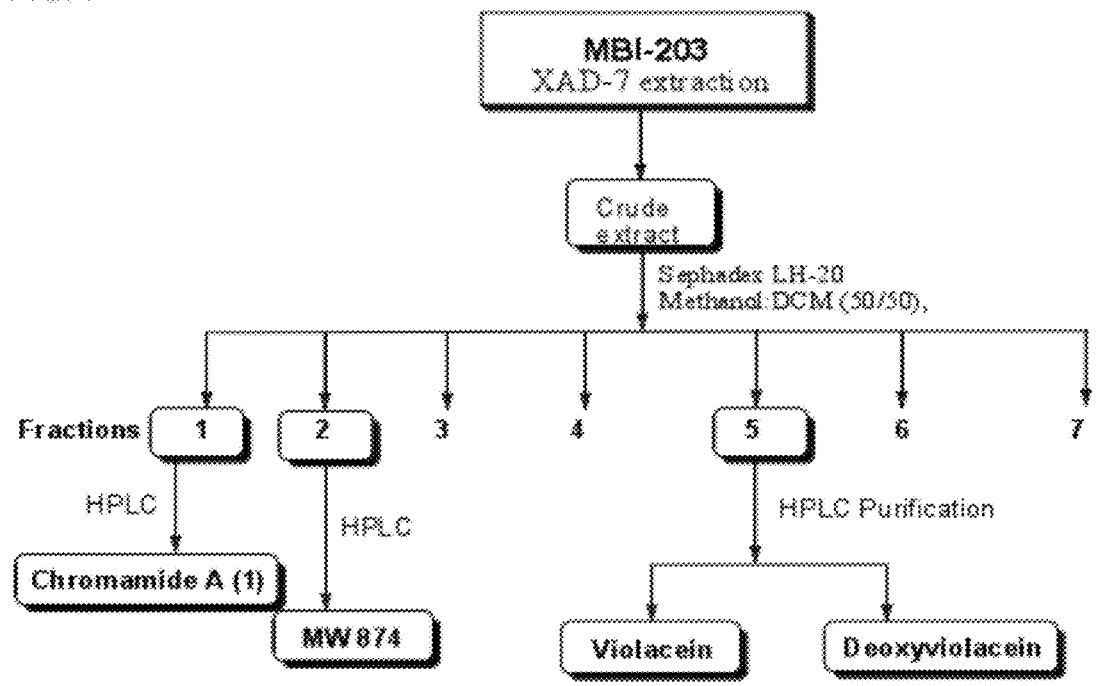
FIG. 1 is a schematic representation of purification scheme for obtaining the compounds of the invention from culture broth.

DETAILED DESCRIPTION OF THE INVENTION

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or medium used to culture or grow said organism.

As defined herein, "whole broth culture" refers to a liquid culture containing both cells and media. If bacteria are grown on a plate the cells can be harvested in water or other liquid, whole culture.

The term "supernatant" refers to the liquid remaining when cells grown in broth or are harvested in another liquid from an agar plate and are removed by centrifugation, filtration, sedimentation, or other means well known in the art.

As defined herein, "filtrate" refers to liquid from a whole broth culture that has passed through a membrane.

As defined herein, "extract" refers to liquid substance removed from cells by a solvent (water, detergent, buffer) and separated from the cells by centrifugation, filtration or other method.

As defined herein, "metabolite" refers to a compound, substance or byproduct of a fermentation of a microorganism, or supernatant, filtrate, or extract obtained from a microorganism that has pesticidal and particularly, insecticidal activity. As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods.

As defined herein, a "carrier" is an inert, organic or inorganic material, with which the active ingredient is mixed or formulated to facilitate its application to plant or other object to be treated, or its storage, transport and/or handling.

The term "modulate" is used to mean to alter the amount of pest infestation or rate of spread of pest infestation.

As defined herein, the term "pest infestation" is the presence of a pest in an amount that causes a harmful effect including a disease or infection in a host population or emergence of an undesired weed in a growth system.

As defined herein, a "pesticide" is a substance derived from a biological product or chemical substance that increase mortality or inhibit the growth rate of plant pests and includes but is not limited to nematocides, insecticides, plant fungicides, plant bactericides, and plant viricides.

As defined herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As defined herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As defined herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As defined herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As defined herein, "aryl" refers to aromatic groups having in the range of 6 up to 14 carbon atoms and "substituted aryl" refers to aryl groups further bearing one or more substituents as set forth above.

As defined herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As defined herein, "alkoxy" refers to the moiety —O-alkyl-, wherein alkyl is as defined above, and "substituted alkoxy" refers to alkoxyl groups further bearing one or more substituents as set forth above.

As defined herein, "thioalkyl" refers to the moiety —S-alkyl-, wherein alkyl is as defined above, and "substituted thioalkyl" refers to thioalkyl groups further bearing one or more substituents as set forth above.

As defined herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As defined herein, "heterocyclic", refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituent's as set forth above.

Methods of Production

As noted above, compounds or metabolites may be obtained, are obtainable or derived from an organism having the identifying characteristics of a *Chromobacterium* species, more particularly, from an organism having the identifying characteristics of a strain of *Chromobacterium substugae*, more particularly from a strain of *Chromobacterium substugae* sp. nov. which may have the identifying characteristics of NRRL B-30655, or alternatively from any other microorganism. The methods comprise cultivating these organisms and obtaining the compounds and/or compositions of the present invention by isolating these compounds from the culture of these organisms.

In particular, the organisms are cultivated in nutrient medium using methods known in the art. The organisms may be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium comprising carbon and nitrogen sources and inorganic salts, using procedures known in the art. Suitable media are available may be available from commercial sources or prepared according to published compositions.

After cultivation, a supernatant, filtrate and/or extract of or derived from *Chromobacterium* sp. may be used in formulating a pesticidal composition.

Alternatively, after cultivation, the compounds and/or metabolites may be extracted from the culture broth.

The extract may be fractionated by chromatography. Chromatographic fractions may be assayed for toxic activity against, for example, Cabbage looper (*Trichoplusia ni*) or Beet armyworm (*Spodoptera exigua*) using methods known in the art. This process may be repeated one or more times using the same or different chromatographic methods.

Compositions

Compositions may comprise whole broth cultures, liquid cultures, or suspensions of a strain from a *Chromobacterium* sp., e.g. a strain having the identifying characteristics of *Chromobacterium substugae* sp. Nov and more particularly, having the identifying characteristics of NRRL B-30655 (see U.S. Pat. No. 7,244,607), as well as supernatants, filtrates or extracts obtained from a strain of a *Chromobacterium* sp., e.g. a strain having the identifying characteristics of *Chromobacterium substugae* sp. Nov and more particularly, having the identifying characteristics of NRRL B-30655 (see U.S. Pat. No. 7,244,607), or the supernatant, filtrate and/or extract or one or more metabolites or isolated compounds derived from a strain of a *Chromobacterium* sp. or combinations of the foregoing which in particular have nematocidal activity.

The compositions set forth above can be formulated in any manner. Non-limiting formulation examples include, but are not limited to, Emulsifiable concentrates (EC), Wettable powders (WP), soluble liquids (SL), Aerosols, Ultra-low volume concentrate solutions (ULV), Soluble powders (SP), Microencapsulation, Water dispersed Granules, Flowables (FL), Microemulsions (ME), Nano-emulsions (NE), etc. In any formulation described herein, percent of the active ingredient is within a range of 0.01% to 99.99%.

The compositions may be in the form of a liquid, gel or solid.

A solid composition can be prepared by suspending a solid carrier in a solution of active ingredient(s) and drying the suspension under mild conditions, such as evaporation at room temperature or vacuum evaporation at 65° C. or lower.

A composition may comprise gel-encapsulated active ingredient(s). Such gel-encapsulated materials can be prepared by mixing a gel-forming agent (e.g., gelatin, cellulose, or lignin) with a culture or suspension of live or inactivated *Chromobacterium*, or a cell-free filtrate or cell fraction of a *Chromobacterium* culture or suspension, or a spray- or freeze-dried culture, cell, or cell fraction or in a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition set forth above may be combined with another microorganism and/or pesticide (e.g., nematocide, fungicide, insecticide). The microorganism may include but is not limited to an agent derived from *Bacillus* sp., *Pseudomonas* sp., *Brevabacillus* sp., *Lecanicillium* sp., non-*Ampelomyces* sp., *Pseudozyma* sp., *Streptomyces* sp, *Burkholderia* sp, *Trichoderma* sp, *Gliocladium* sp. Alternatively, the agent may be a natural oil or oil-product having fungicidal and/or insecticidal activity (e.g., paraffinic oil, tea tree oil, lemongrass oil, clove oil, cinnamon oil, citrus oil, rosemary oil, pyrethram). Furthermore, the pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, an anthranilic diamide (e.g., chlorantranilipole) and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a Reynoutria extract.

The fungicide can also be a multi-site non-inorganic, chemical fungicide selected from the group consisting of chloronitrile, quinoxaline, sulphamide, phosphonate, phosphite, dithiocarbamate, chloralkylhios, phenylpyridin-amine, cyano-acetamide oxime.

The composition may as noted above, further comprise an insecticide. The insecticide may include but is not limited to avermectin, Bt (e.g., *Bacillus thuringiensis* var. *kurstaki*), neem oil, spinosads, *Burkholderdia* sp. as set forth in WO2011/106491, entomopathogenic fungi such a *Beauveria bassiana* and chemical insecticides including but not limited to organochlorine compounds, organophosphorous compounds, carbamates, pyrethroids, pyrethrins and neonicotinoids.

As noted above, the composition may further comprise a nematocide. This nematocide may include, but is not limited to, avermectin, microbial products such as Biome (*Bacillus firmus*), *Pasteuria* spp and organic products such as saponins.

The compositions may be applied using methods known in the art. Specifically, these compositions may be applied to plants or plant parts. Plants are to be understood as meaning in the present context all plants and plant populations such as desired and undesired wild plants or crop plants (including naturally occurring crop plants). Crop plants can be plants, which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, off-shoots and seeds.

Treatment of the plants and plant parts with the compositions set forth above may be carried out directly or by allowing the compositions to act on their surroundings, habitat or storage space by, for example, immersion, spraying, evaporation, fogging, scattering, painting on, injecting. In the case that the composition is applied to a seed, the composition may be applied to the seed as one or more coats prior to planting the seed using one or more coats using methods known in the art.

Uses

The compositions, cultures, supernatants, metabolites and pesticidal compounds set forth above may be used as pesticides. In particular, the compositions, cultures, supernatants, metabolites and pesticidal compounds as set forth above may be used as insecticides and nematocides, alone or in combination with one or more pesticidal substances set forth above.

Specifically, nematodes that may be controlled using the method set forth above include but are not limited to parasitic nematodes such as root-knot, cyst, and lesion nematodes, including but not limited to *Meloidogyne* sp. *Tylenchorhynchus* sp, *Hoplolaimus* sp., *Helicotylenchus* sp., *Pratylenchus* sp., *Heterodera* sp., *Globodera*, sp., *Trichodorus* sp. *Paratrichodorus* sp., *Xiphinema* sp., and *Criconema* sp.; particularly *Meloidogyne incognita* (root knot nematodes), as well as *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Phytopathogenic insects controlled by the method set forth above include but are not limited to non-Culicidae larvae insects from the order (a) Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp., *Diparopsis castanea*, *Earias* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; (b) Coleoptera, for example, *Agriotes* spp., *Anthonomus* spp.,

*Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.; (c) *Orthoptera*, for example, *Blatta* spp., *Blattella* spp., *Gryllotalpa* spp., *Leucophaea maderae, Locusta* spp., *Periplaneta* spp. and *Schistocerca* spp.; (d) *Isoptera*, for example, *Reticulitermes* spp.; (e) *Psocoptera*, for example, *Liposcelis* spp.; (f) *Anoplura*, for example, *Haematopinus* spp., *Linognathus* spp., *Pediculus* spp., *Pemphigus* spp. and *Phylloxera* spp.; (g) *Mallophaga*, for example, *Damalinea* spp. and *Trichodectes* spp.; (h) *Thysanoptera*, for example, *Frankliniella* spp., *Hercinotnrips* spp., *Taeniothrips* spp., *Thrips palmi, Thrips tabaci* and *Scirtothrips aurantii*; (i) *Heteroptera*, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Tniatoma* spp.; (j) *Homoptera*, for example, *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*; (k) *Hymenoptera*, for example, *Acromyrmex, Atta* spp., *Cephus* spp., *Diprion* spp., *Diprionidae, Gilpinia polytoma, Hoplocampa* spp., *Lasius* spp., *Monomorium pharaonic, Neodiprion* spp., *Solenopsis* spp. and *Vespa* spp.; (l) *Diptera*, for example, *Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.; (m) *Siphonaptera*, for example, *Ceratophyllus* spp. and *Xenopsylla cheopis* and (n) from the order Thysanura, for example, *Lepisma saccharina*. The active ingredients according to the invention may further be used for controlling crucifer flea beetles (*Phyllotreta* spp.), root maggots (*Delia* spp.), cabbage seedpod weevil (*Ceutorhynchus* spp.) and aphids in oil seed crops such as canola (rape), mustard seed, and hybrids thereof, and also rice and maize. In a particular embodiment, the insect may be a member of the *Spodoptera*, more particularly, *Spodoptera exigua, Myzus persicae, Plutella xylostella* or *Euschistus* sp.

Application of an effective pesticidal control amount of a supernatant, filtrate or extract containing a pesticidally active metabolite, or isolated compound produced by the *Chromobacterium* sp. or application of combinations of the foregoing is provided. The strain or supernatant or filtrate or extract, metabolite and/or compound are applied, alone or in combination with another pesticidal substance, in an effective pest control or pesticidal amount. An effective amount is defined as that quantities of microorganism cells, supernatant, filtrate or extract, metabolite and/or compound alone or in combination with another pesticidal substance that is sufficient to modulate pest infestation. The effective rate can be affected by pest species present, stage of pest growth, pest population density, and environmental factors such as temperature, wind velocity, rain, time of day and seasonality. The amount that will be within an effective range in a particular instance can be determined by laboratory or field tests.

EXAMPLES

The composition and methods set forth above will be further illustrated in the following, non-limiting Examples. The examples are illustrative of various embodiments only and do not limit the claimed invention regarding the materials, conditions, weight ratios, process parameters and the like recited herein.

Example 1

Extraction of Compounds from *Chromobacterium Substugae*

The following procedure is used for the purification of compounds extracted from the culture of *Chromobacterium substugae*:

The culture broth derived from the 10-L fermentation *C. substugae* in L-broth is extracted with Amberlite XAD-7 resin (Asolkar et al., 2006) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone/methanol (50/50) after which the acetone/methanol is filtered and dried under vacuum using rotary evaporator to give the crude extract. The crude extract is then fractionated by using Sephadex LH 20 size exclusion chromatography ($CH_2Cl_2$/$CH_3OH$; 50/50) to give 7 fractions (FIG. 1). These fractions are then concentrated to dryness using rotary evaporator and the resulting dry residues are screened for biological activity using a feeding assay with Cabbage looper (*Trichoplusia ni*) or Beet armyworm (*Spodoptera exigua*). The active fractions are then subjected to reversed phase HPLC (Spectra System P4000 (Thermo Scientific) to give pure compounds, which are then screened in above mentioned bioassays to locate/identify the active compounds. To confirm the identity of the compound, additional spectroscopic data such as LC/MS and NMR is recorded.

Chromamide A (1) and compound B were isolated from fractions 1 and 2 respectively, whereas violacein (2) & deoxyviolacein (3) were isolated from fraction 5, all of which were obtained from Sephadex LH 20 chromatography. The structures of these compounds are set forth in FIG. 7.

Purification of Compounds

Purification of chromamide A (1) was performed by using HPLC C-18 column (Phenomenex, Luna 10u C18(2) 100 A, 250×10), water:acetonitrile gradient solvent system (0-10 min, 80-75% aqueous $CH_3CN$; 10-45 min, 75-60% aqueous $CH_3CN$; 45-55 min, 60-50% aqueous $CH_3CN$; 55-65 min, 50-100% aqueous $CH_3CN$; 65-70 min, 100% $CH_3CN$; 55-70 min, 0-80% aqueous $CH_3CN$) at 2.5 mL/min flow rate and UV detection of 210 nm. The active compound chromamide A (1), has retention time 23.19 min.

Purification of invention compound B was performed by using HPLC C-18 column (Phenomenex, Luna 10u C18 (2) 100 A, 250×10), water:acetonitrile gradient solvent system (0-10 min, 80-75% aqueous $CH_3CN$; 10-45 min, 75-60% aqueous $CH_3CN$; 45-55 min, 60-50% aqueous $CH_3CN$;

Figure 6:
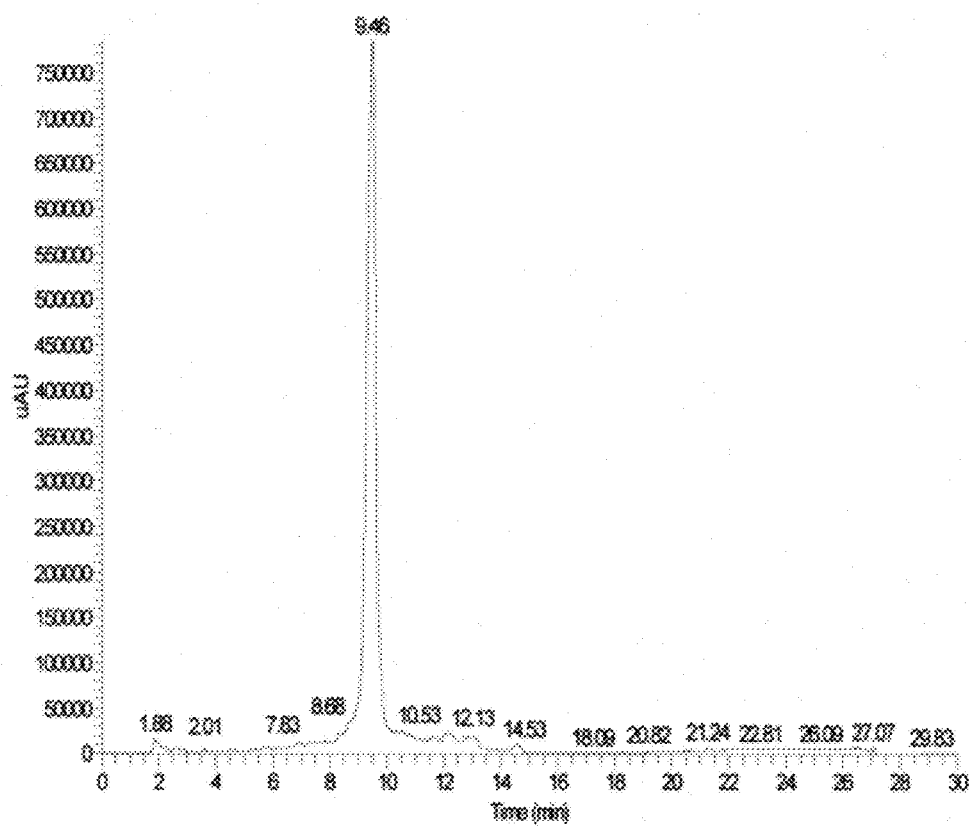
FIG. 6 depicts the HPLC chromatogram for compound B (MW 874).

55-65 min, 50-100% aqueous CH$_3$CN; 65-70 min, 100% CH$_3$CN; 55-70 min, 0-80% aqueous CH$_3$CN) at 2.5 mL/min flow rate and UV detection of 210 nm, the active compound B, retention time 26.39 min (see FIG. 6).

Purification of violacein (2) and deoxyviolacein (3) were performed by using HPLC C-18 column (Phenomenex, Luna 10u C18(2) 100 A, 250×10), water:acetonitrile gradient solvent system (0-10 min, 70-60% aqueous CH$_3$CN; 10-40 min, 60-20% aqueous CH$_3$CN; 40-60 min, 20-0% aqueous CH$_3$CN; 60-65 min, 100% CH$_3$CN; 65-75 min, 0-70% aqueous CH$_3$CN) at 2.5 mL/min flow rate and UV detection of 210 nm, the active compounds violacein (2), had a retention time 7.86 min and deoxyviolacein (3) retention time 12.45 min.

Mass Spectroscopy Analysis of Compounds

Figure 2:
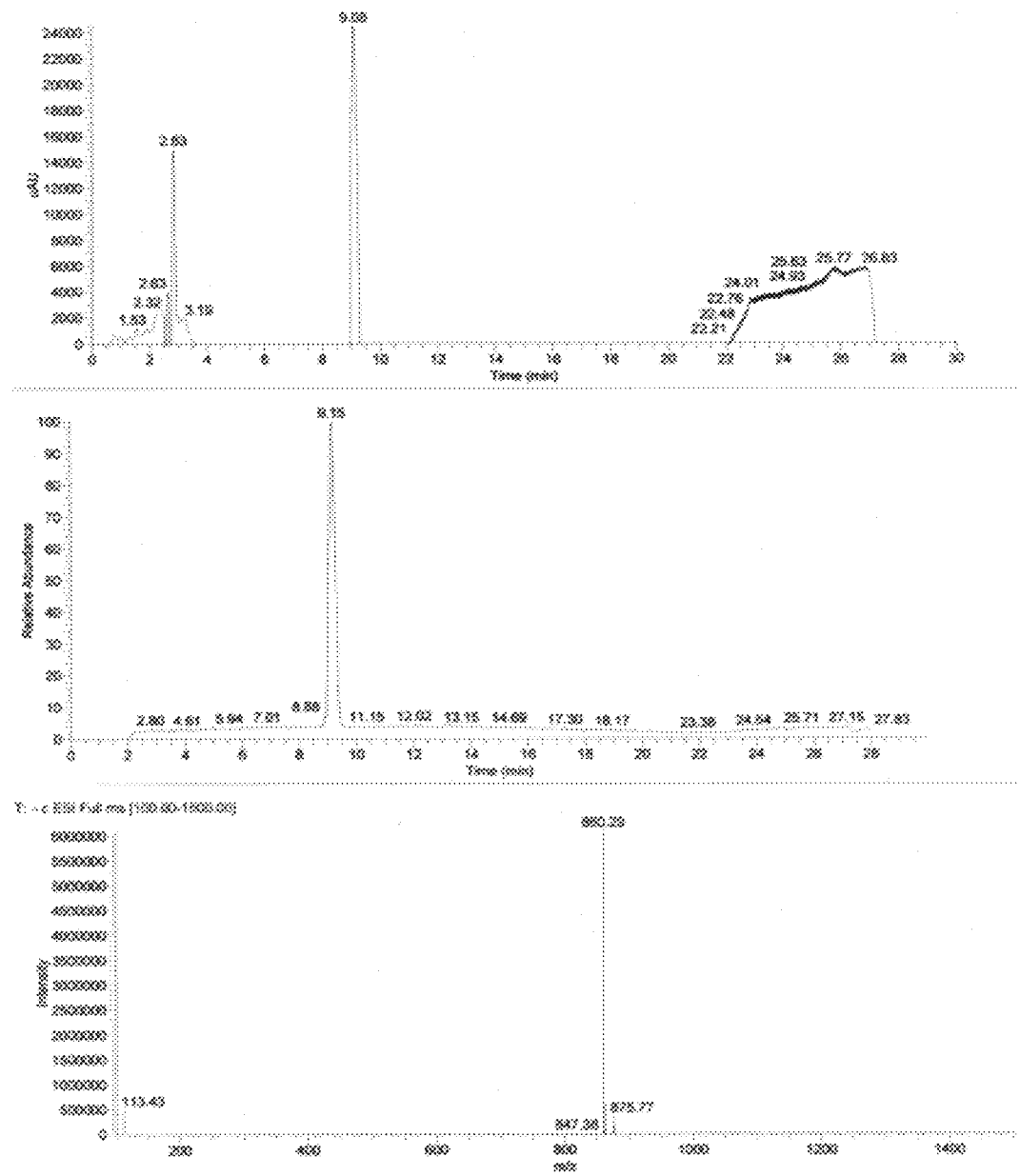
FIG. 2 depicts the ESI-LCMS chromatogram for chromamide A (1).

Mass spectroscopy analysis of active peaks is performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5µ 100 A column (Phenomenex). The solvent system consisted of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 µL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The chromamide A (1) has a molecular mass of 860 in positive ionization mode (see FIG. 2). The LC-MS chromatogram for another active compound B suggests a molecular mass of 874 in positive ionization mode. Violacein (2) and deoxyviolacein (3) had the molecular masses of 313 and 327 respectively in positive ionization mode.

NMR Spectroscopy Analysis of Compounds

NMR-NMR spectra were measured on a Bruker 600 MHz gradient field spectrometer. The reference is set on the internal standard tetramethylsilane (TMS, 0.00 ppm). The amino acid analyses were carried out on Hitachi 8800 amino acid analyzer.

Figure 3:
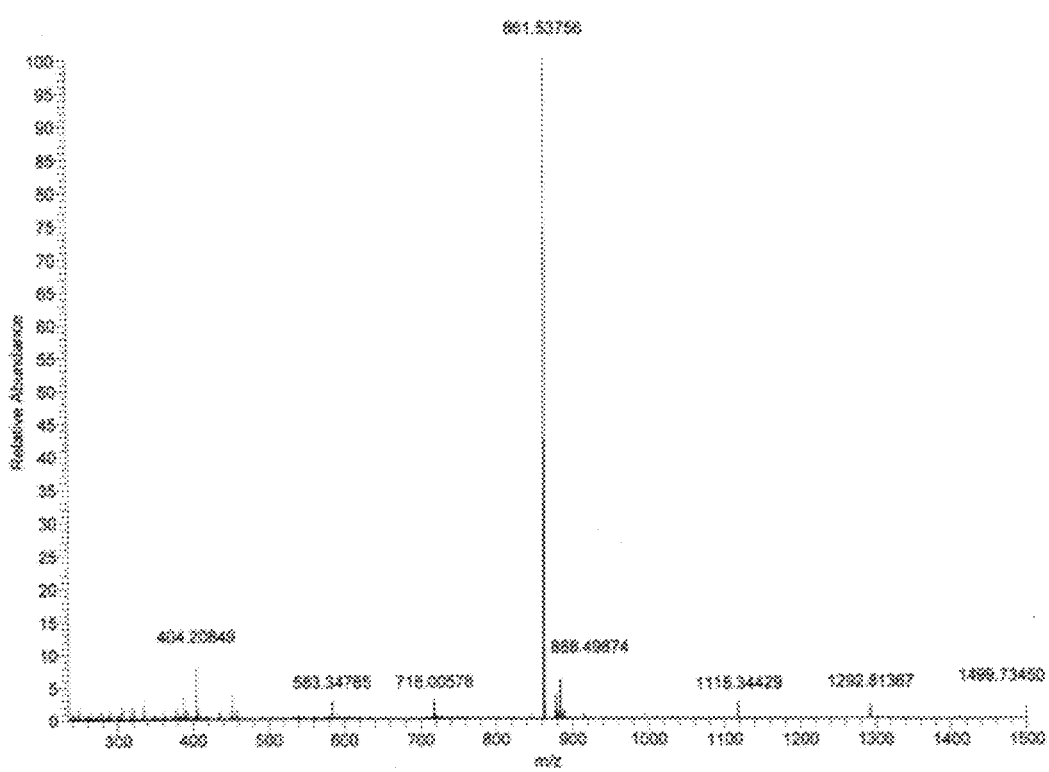
FIG. 3 depicts the HRMS data for chromamide A (1).
Figure 4:
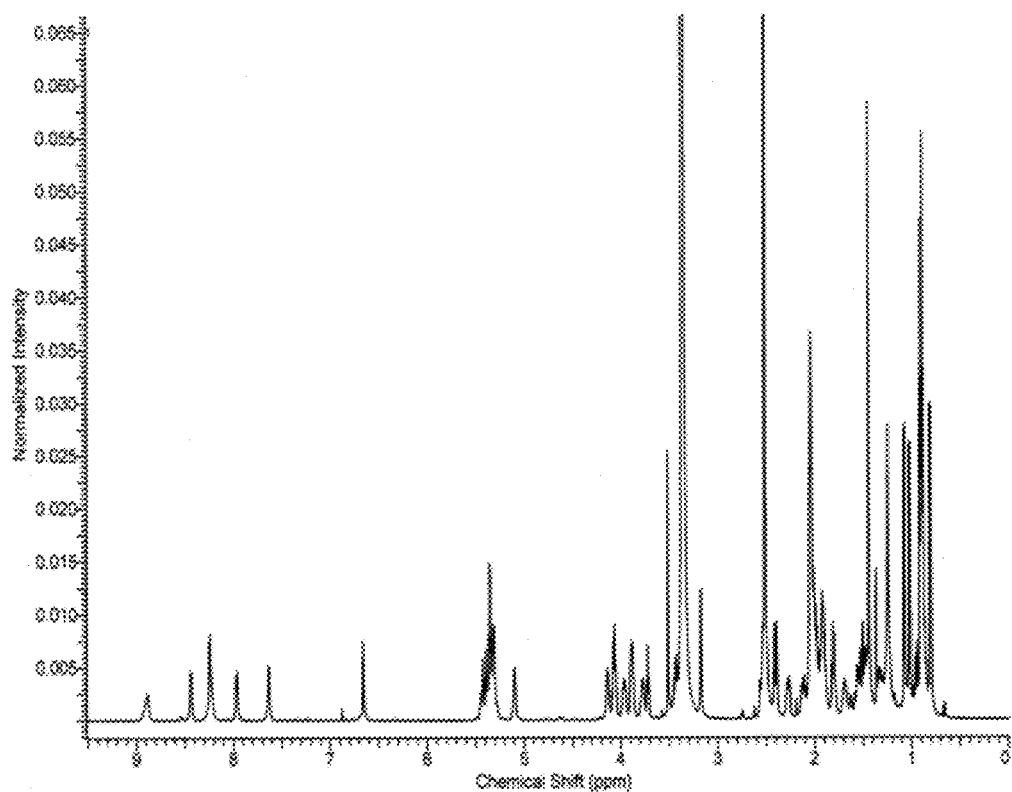
FIG. 4 depicts $^1H$ NMR for chromamide A (1) in DMSO-$d_6$ at 600 MHz.
Figure 5:
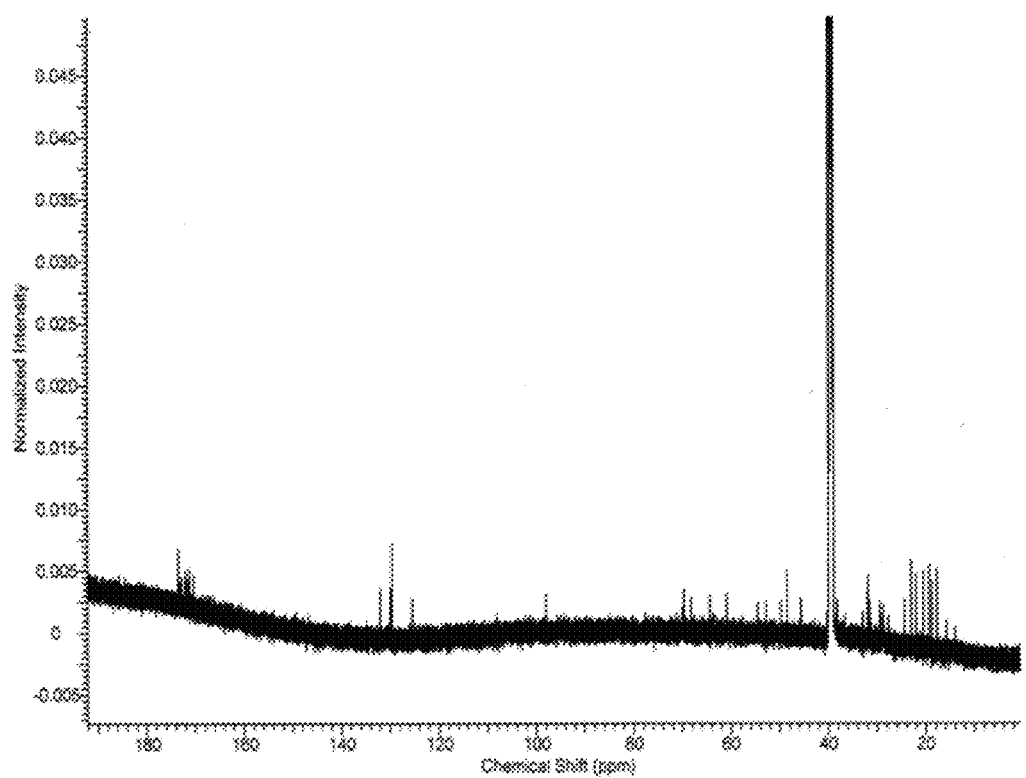
FIG. 5 depicts $^{13}C$ NMR for chromamide A (1) in DMSO-$d_6$ at 600 MHz.

For structure elucidation, the purified chromamide A with molecular weight 860 is further analyzed using a 600 MHz NMR instrument, and has $^1$H NMR δ values at 8.89, 8.44, 8.24, 8.23, 7.96, 7.63, 6.66, 5.42, 5.36, 5.31, 5.10, 4.13, 4.07, 4.05, 3.96, 3.95, 3.88, 3.77, 3.73, 3.51, 3.44, 3.17, 2.40, 2.27, 2.11, 2.08, 2.03, 2.01, 1.97, 1.95, 1.90, 1.81, 1.68, 1.63, 1.57, 1.53, 1.48, 1.43, 1.35, 1.24, 1.07, 1.02, 0.96, 0.89, 0.88, 0.87, 0.80 (see FIG. 4) and has $^{13}$C NMR values of 173.62, 172.92, 172.25, 172.17, 171.66, 171.28, 170.45, 132.13, 130.04, 129.98, 129.69, 129.69, 125.48, 98.05, 70.11, 69.75, 68.30, 68.25, 64.34, 60.94, 54.54, 52.82, 49.72, 48.57, 45.68, 40.38, 39.90, 38.18, 36.60, 31.98, 31.62, 31.58, 29.53, 28.83, 27.78, 24.41, 23.06, 22.09, 20.56, 19.31, 18.78, 17.66, 15.80 (see FIG. 5). The chromamide A was isolated as a white solid, which analyzed for the molecular formula C$_{43}$H$_{68}$N$_6$O$_{12}$ (13 degrees of unsaturation), by ESI high-resolution mass spectrometry (obsd M$^+$ m/z 861.5376, calcd M$^+$ m/z 861.5343) (FIG. 3). The $^1$H NMR spectral data of chromamide A in DMSO-d$_6$ exhibited 68 proton signals, in which nine protons [δ$_H$: 8.89, 8.44, 8.23, 8.22, 7.96, 7.64, 6.65, 5.10, 4.13], were assigned as either NH or OH due to lack of carbon correlation in a heteronuclear correlation NMR(HMQC) analysis. The $^{13}$C NMR spectrum, showed seven carbonyl signals [δ$_C$: 173.62, 172.92, 172.25, 1.72.17, 171.66, 171.28, 170.45] and in the $^1$H NMR spectrum, six characteristic α-amino protons signals [δ$_H$: 4.07, 4.06, 3.96, 3.95, 3.88, 3.72] were observed which demonstrate that chromamide A is a peptide.

Interpretation of 2D NMR data led to the assignment of three amino acid units of the six, one leucine (Leu), one valine (Val) and one glutamine (Gln). The presence of these amino acids were confirmed by results of amino acid analysis, which also showed the presence of the above three amino acids. Further analysis of DEPT and 2D NMR spectral data (COSY, HSQC and HMBC) established the presence three sub-structures I, II and III as showed below.

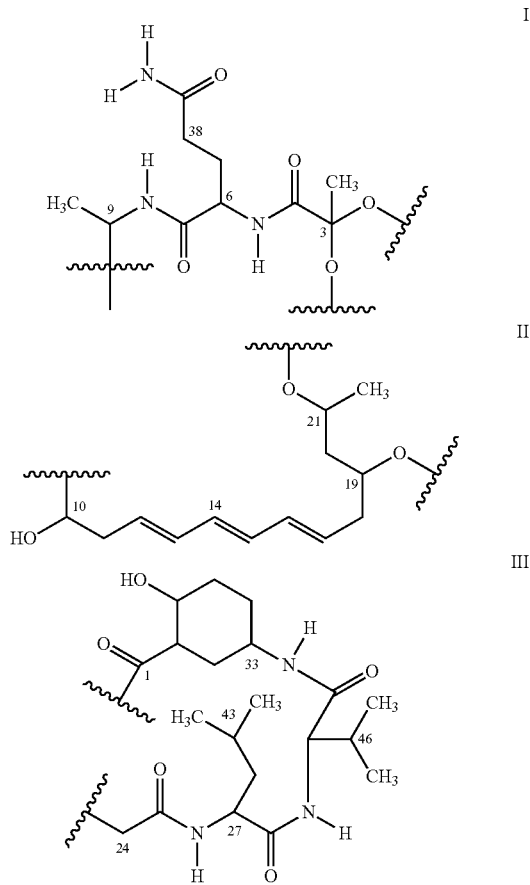

The connections of the three sub-structures in 1 were accomplished by routine HMBC NMR analysis using correlations between the α-amino proton and/or the secondary amide proton and the carbonyl carbon resonances and chemical shift consideration. The linkage of C-9 from sub-structure I to C-10 from sub-structure II was established by HMBC correlations from CH$_3$-40 [δ$_H$: 1.00] and the α-amino proton of alanine [δ$_H$: 3.42] to the C-10 carbon [δ$_C$: 70.11]. This was further confirmed by the three bond HMBC correlation from hydroxyl at [δ$_H$: 5.10] to C-9 at [δ$_C$: 49.78]. The methylene at [δ$_H$: 3.50] from sub-structure III showed a three bond HMBC correlation to C-19 [δ$_C$: 68.31] which connected the sub-structure I and II. The quaternary carbon at C-3 [$\delta_C$: 98.09] was connected to C-21 [$\delta_C$: 64.40] through a weak correlation from H-21 [$\delta_H$: 3.95] together with their chemical shift values to form a one ring system. Lastly, the ring closure linkage was secured by a three-bond HMBC correlation from H$_3$-36 [$\delta_H$: 1.43] to C-1 [$\delta_C$: 172.17], which allowed the planar structure of chromamide A (1) to be assigned.

The compound B with a molecular weight 874 exhibited similar NMR and UV data suggesting that this compound B also belongs to the class of peptide.

Figure 7:
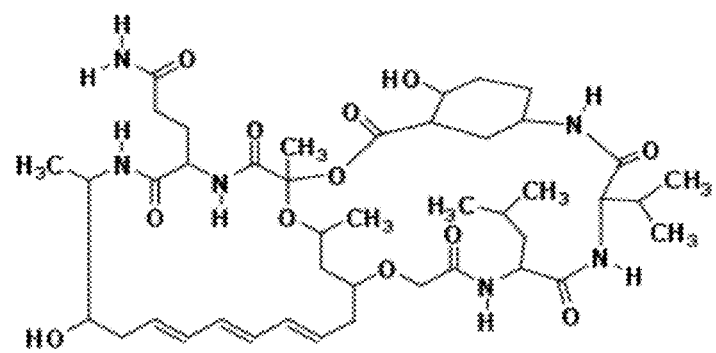
FIG. 7 depicts chemical structures for chromamide A (1) violacein (2) and deoxyviolacein (3).
Figure 7:
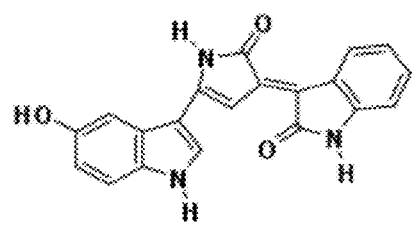
Figure 7:
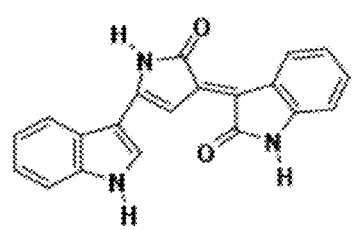

The structure for violacein (2) and deoxyviolacein (3) was assigned by comparison of the data of these compounds with those published in the literature. The structures of chromamide A, violacein and deoxyviolacein are shown in FIG. 7.

Example 2

Amino Acids Analysis of Chromamide A

Chromamide A (0.05 mg) was hydrolyzed by using liquid phase hydrolysis (6N HCL, 1% Phenol, 110° C., 24 hr., in vacuum). After cooling, the reaction mixture was dried and the hydrolyzed product was dissolved in Norleu dilution buffer to 1.0 mL volume. A 50 µl of the sample was loaded onto the ion-exchange column for analysis.

For standards and calibration, an amino acid standards solution for protein hydrolysate on the Na-based Hitachi 8800 (Sigma, A-9906) is used to determine response factors, and thus calibrate the Hitachi 8800 analyzer for all of the amino acids. Each injection contains NorLeucine as an internal standard to allow correction of the results for variations in sample volume and chromatography variables. System utilizes Pickering Na buffers, Pierce Sequanal grade HCl (hydrolysis), a Transgenomic Ion-Exchange column and an optimized method developed by Molecular Structure Facility (MSF), UC Davis, and the individual amino acid present in the sample are reported. The amino acids present in the sample (chromamide A) were found to be Glx (Glutamine/Glutamic acid), leu (leucine) and Val (Valine).

Example 3

Confirmation of Toxicity on Cabbage Looper (*Trichoplusia ni*)

Toxicity of the compound of interest in fraction 1 (F1) was confirmed in an in vitro assay using 1$^{st}$ instar cabbage looper larvae as a test object.

Two hundred microliters of commercial cabbage looper diet was distributed in each well of a 96-well microplate. After the diet had solidified, 100 uL of solution containing 50 uL of extract (corresponding to four individual peaks found in fraction 1; H1-H4), 350 uL EtOH and 600 uL sterile DI water was pipetted in each well, after which the plate was dried using a hand-held fan. The amount of extract in each well was 10 micrograms. Each treatment was replicated eight times, and a mixture of pure ethanol and water was used as a negative control.

One test insect (1$^{st}$ instar larvae of cabbage looper) was placed in each well, and the plate was covered with an adhesive seal. The seal was punctured for aeration, and the sealed plate was incubated at 26° C. for four days.

The results presented in Table 1 below show good activity (>60% mortality) with a compound in peak H1. This particular peak corresponds with the chromamide A (1) (FIG. 1).

TABLE 1

Cabbage Looper Mortality (%) at 10 ug/well

| Fraction | % Mortality |
|---|---|
| F1 H1 | 66.7 |
| F1 H2 | 11.1 |
| F1 H3 | 33.3 |
| F1 H4 | 11.1 |

Example 4

Determination of LC$_{50}$ for Violacein for Cabbage Looper (*Trichoplusia ni*)

The 96-well plate assay system described in the previous example was used to determine the concentration of pure violacein needed to kill 50% of the 1$^{st}$ instar cabbage looper larvae. The mortality values recorded after 4 days of incubation at 26° C. are presented in Table 2 below. Based on the data, violacein is a potent insecticide with an estimated LC$_{50}$ value of $7*10^{-6}$ micrograms per well for cabbage looper larvae in an in vitro diet-overlay assay.

TABLE 2

Effect of Violacein on Cabbage Looper Mortality

| Violacein ug/well | % mortality Day 4 |
|---|---|
| 10 | 100 |
| 1 | 100 |
| 0.1 | 100 |
| 0.01 | 100 |
| 0.001 | 100 |
| 0.0001 | 100 |
| 0.00001 | 71.4 |
| 0.000001 | 14.2 |
| 1E−07 | 0 |

Example 5

Nematicidal Activity of *Chromobacterium substugae* (MBI-203) Broth on Juvenile Root-Knot Nematodes To assess the effect of filter-sterilized *C. substugae* on the motility (and subsequent recovery) of juvenile (J2) root-knot nematodes (*Meloidogyne incognita* VW6), the following test was conducted on 24-well plastic cell-culture plates:

A 300-ul aliquot of each test solution (either 1× or 0.1× filter-sterilized broth) was added into appropriate wells after which, fifteen nematodes dispensed in 10 ul of DI water were added into each well, plate was closed with a lid, and incubated at 25° C. for 24 hours. Water and Avid (avermectin) at 20,000× dilution were used as negative and positive controls, respectively. Effect of each compound on nematode mobility was checked after 24 hours by probing each nematode with a needle, and the proportion of immobile nematodes in each treatment was recorded in a notebook using a % scale. To assess the recovery of mobility in each treatment, a volume of 200 ul was removed from each well, and the remaining solution in each well was diluted by adding 2 mL of DI water. Plates were again incubated for 24 hours as described above, after which the second mobility evaluation (48-hour) was performed.

Figure 8:
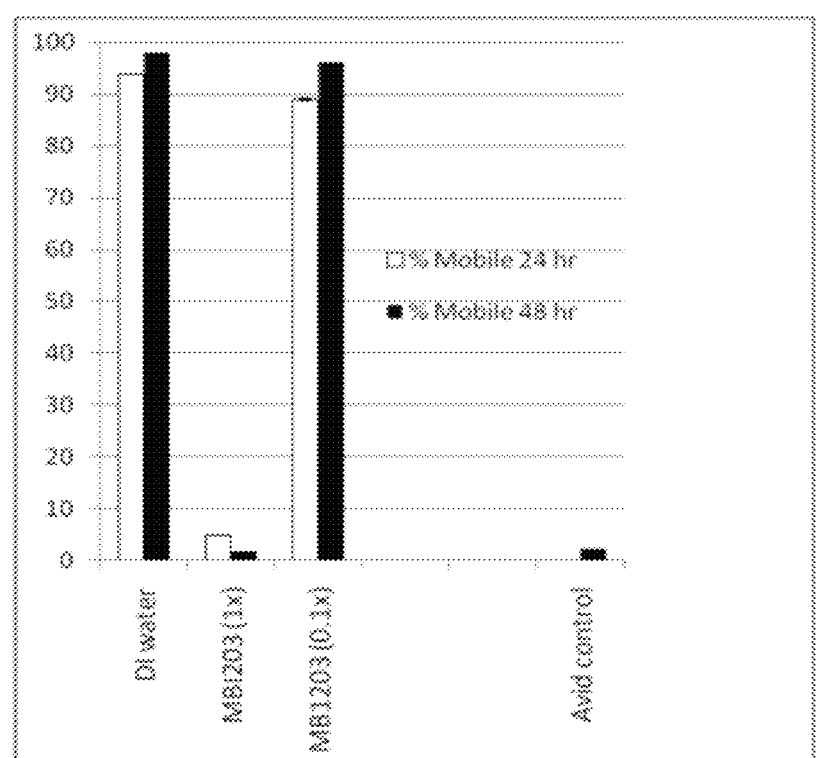
FIG. 8 Percentage of mobile nematodes after treatment with filter sterilized *C. substugae* broth (1×—undiluted; 0.1×—diluted 10-fold) after 24 hours.
Figure 9:
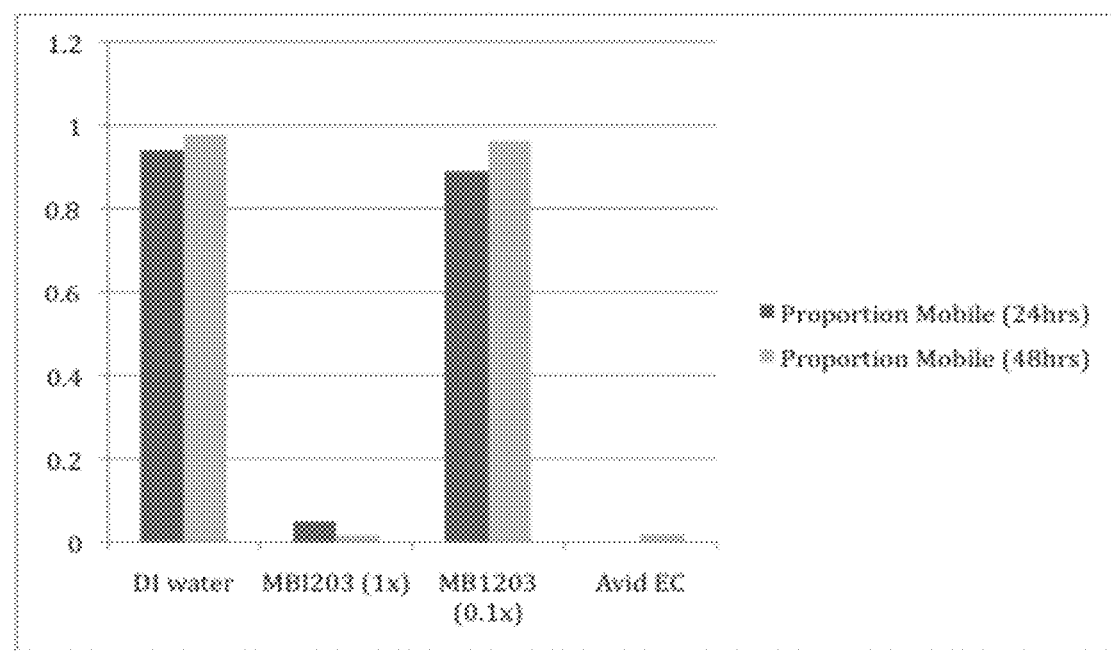
FIG. 9 Percentage of mobile nematodes after treatment with filter sterilized *C. substugae* broth (1×—undiluted; 0.1×—diluted 10-fold) after 48 hours.

The results presented in FIGS. 8 and 9 show that the undiluted filter-sterilized broth can immobilize the free-living juvenile root-knot nematodes. This effect lasts at least for 48-hours, which suggests that *C. substugae* broth has nematicidal activity.

Example 6

Effect of *Chromobacterium substugae* (MBI-203) Broth on Galling of Cucumber Roots MBI-203 was tested for its intrinsic activity against the root knot nematode *Meloidogyne* sp. in two mini drench tests.
Materials and Methods
Specifically MBI-203 was tested in a greenhouse assay conducted in 45 ml pots. Cucumber seeds cv. Toshka were sown directly into pots filled with a sandy loam soil. Ten days later pots were each treated with 5 ml of a suspension. Hereafter, pots were inoculated with 3000 eggs of *M. incognita*. Four replicates were prepared for each treatment and rate. The trial was harvested fourteen days after trial application and inoculation. Root galling was assessed according to Zeck's gall index (Zeck, 1971). Specific conditions are set forth below in Table 3.

Phytotoxicity was measured as a reduction of growth of the emerged cucumber seedling in comparison to the control.

TABLE 3

| | MBI-203 Fosthiazate (Standard, EC 150) |
|---|---|
| Test species | *Meloidogyne* sp. applied at 3000 eggs per mini drench pot (in 2 ml) |
| Test plant | *Cucumis sativus* (cucumber cv. Toschka) |
| Test formulation | MBI-203 = 96% liquid formulation |
| Test concentrations for MBI-203 | Mini-drench test #1: 100, 50 ml/L<br>Mini-drench test #2: 50, 25, 12.5, 6, 3, 1.5 ml/L |
| Test application | Drench application |

Results
Mini Drench Test No. 1
The activity of the treatments was very high and a reduction of almost 100% was observed when applied at a concentration of 50 ml/L (MBI-203). Minor phytotoxicity was observed for MBI-203. Fosthiazate performed as usual (100% control at 20 ppm).
Mini Drench Test No. 2
MBI-203 showed phytotoxicity at the highest concentrations of 50 and 25 ml/L and assessments could not be made at these rates.
At a concentration of 12.5 ml/L nematode control was over 95% which decreased to 33% at 3 ml/L. At a rate of 1.5 ml/L no activity was recorded.
Fosthiazate performed as usual (100% control at 20 ppm).

Example 8

Synergistic Studies with *Chromobacterium substugae* (MBI-203) Broth

Synergy tests were performed by treating artificial diet in 96-well plates and feeding treated diet to neonate larvae. 100 μL of treatment were pipetted into multiple wells of each plate. MBI-203 (whole cell broth concentrated to 7.6% dry cell weight) alone, the commercial insecticide alone, and the combination of the 2 were tested using predetermined $LC_{50}$ concentrations or fractions thereof. The diet was fan-dried to remove excess moisture. Neonate Beet Armyworm, *Spodoptera exigua*, or Cabbage Loopers, *Trichoplusia ni*, were transferred into each well of the multi-well plate. Infested plates were covered with adhesive plate sealer and a single small hole was poked into the sealer over each well to allow for aeration. Plates were stored in an incubator at 26° C., 16 h light/8 h dark cycle for 3 days. On the third and fourth day after infesting, mortality was scored.

The determination of a synergistic, antagonistic, or additive interaction was determined using the methods from (Colby 1967). Due to variation in bioassays, it was determined that ratios between 0 and 0.9 would be considered antagonistic, 0.9-1.1 ratios would be additive, and ratios above 1.1 would be considered synergistic relationships.

MBI-203 synergy with insecticides against Cabbage Loopers was tested. Chlorantranilipole (marketed as Coragen®, Dupont), *Bacillus thuringiensis* var. *kurstaki* (Dipel®, Valent Biosciences), Spinosad (marketed as Entrust®, Dow Agro Sciences), Spirotetramet (marketed as Movento®, Bayer Crop Science) and Pyrethrum/pyrethrins (marketed as Pyganic®, Arbico Organics) were tested with MBI-203. As noted above, except where indicated, $LC_{50}$ concentrations of MBI-203 and insecticides were used. The results are shown in Table 4. All, but Bt var. *kurstaki* and 1 instance of $LC_{50}$ concentration showed synergism.

TABLE 4

MBI-203 + Insecticide: Effect on cabbage loopers

| Product | MBI-203 alone Kill % | Product alone Kill % | Calculated Combo Kill % | Actual Combo Kill % | Ratio | Defined relation[a] |
|---|---|---|---|---|---|---|
| Chlorantranilipole | 21 | 3 | 23.4 | 33.3 | 1.42 | syn |
| Bt var. *kurstaki* | 61.7 | 89.6 | 96 | 100 | 1.04 | add |
| Spinosad | 41.5 | 54.3 | 72.99 | 100.00 | 1.37 | syn |
| Spirotetramet | 87.9 | 23.8 | 86.34 | 89.87 | 1.04 | add |
| Spirotetramet (0.5X $LC_{50}$); MBI-203 (0.3X $LC_{50}$) | 90.6 | 41.5 | 91.90 | 94.94 | 1.03 | add |
| Pyrethrum | 19.7 | 2.8 | 21.93 | 55.37 | 2.53 | syn |

[a]syn = synergistic; add = additive

MBI-203 synergy with insecticides against Beet Army Worm (BAW) was tested. Chlorantranilipole (marketed as Coragen®, Dupont), *Bacillus thuringiensis* var. *kurstaki* (Dipel®, Valent Biosciences), Spinosad (marketed as Entrust®, Dow Agro Sciences), Spirotetramet (marketed as Movento®, Bayer Crop Science) and Pyrethrum/pyrethrins (marketed as Pyganic®, Arbico Organics) were tested with MBI-203. As noted above, except where indicated, $LC_{50}$ concentrations of MBI-203 and insecticides were used. The results are shown in Table 5. MBI-203 and Chlorantranilipole interacted additively while *Bacillus thuringiensis* var. *kurstaki* and Spinosad showed synergistic control of BAW with MBI-203. Pyrethrum combinations with MBI-203 were antagonistic. Spirotetramet and MBI-203 combinations were primarily antagonistic against Beet Armyworm.

TABLE 5

MBI-203 + Insecticide: Effect on Beet Armyworm

| Product | MBI-203 alone Kill % | Product alone Kill % | Calculated Combo Kill % | Actual Combo Kill % | Ratio | Defined relation[a] |
|---|---|---|---|---|---|---|
| Chlorantranilipole | 11.6 | 9.1 | 19.69 | 19.9 | 1.01 | add |
| Bt var. *kurstaki* | 24.5 | 19.8 | 39.4 | 68.3 | 1.73 | syn |
| Spinosad | 23.8 | 68.7 | 83.33 | 100 | 1.2 | syn |
| Spirotetramet | 0 | 21.6 | 36.10 | 27.60 | 0.76 | antag |
| Spirotetramet (0.53X $LC_{50}$); MBI-203 (0.7X $LC_{50}$) | 0 | 42.9 | 38.55 | 41.67 | 1.08 | add |
| Spirotetramet | 21.4 | 53.3 | 60.57 | 53.70 | 0.89 | antag |
| Spirotetramet (1.4X $LC_{50}$); MBI-203 (1.2X $LC_{50}$) | 10 | 77.5 | 78.22 | 41.23 | 0.53 | antag |
| Pyrethram | 14.4 | 74.5 | 78.17 | 12.16 | 0.16 | antag |
| Pyrethram | 70.7 | 11.1 | 73.97 | 27.78 | 0.38 | antag |

[a]syn = synergistic; add = additive; antag = antagonistic

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

REFERENCES

Asolkar, R. N., Jensen, P. R., Kauffman, C. A., Fenical, W. 2006. Daryamides A-C, Weakly Cytotoxic Polyketides from a Marine-Derived Actinomycete of the Genus *Streptomyces* strain CNQ-085 *J. Nat. Prod.* 69:1756-1759.

Arena, J. P., K. K. Liu, et al. (1995). "The mechanism of action of avermectins in *Caenorhabditis elegans*—correlation between activation of glutamate-sensitive chloride current, membrane binding and biological activity." *Journal of Parasitology* 81: 286-294.

Balibar, C. J. and C. T. Welsh (2006). "In Vitro Biosynthesis of Violacein from L-Tryptophan by the Enzymes VioA-E from *Chromobacterium violaceum*." *Biochemistry* 45: 15444-15457.

Chalvet-Monfray, K., P. Sabatier, et al. (1996). "Synergy between deltamethrin and prochloraz in bees: Modeling approach." *Environmental Toxicology and Chemistry* 15(4): 525-534.

Chitwood, D. J. (2003). Nematicides. *Encyclopedia of Agrochemicals, vol* 3. J. R. Plimmer. New York, John Wiley & Sons. 3: 1104-1115.

Colby, S. R. (1967). "Calculating Synergistic and Antagonistic Responses of Herbicide Combinations." *Weeds* 15(1): 20-22.

Durán, N., G. Z. Justo, et al. (2007). "Minireview. Violacein: properties and biological activities." *Biotechnol. Appl. Biochem.* 48: 127-133.

Durán, N. and C. F. M. Menck (2001). "*Chromobacterium violaceum*: a review of pharmacological and industrial perspectives." *Crit. Rev. Microbiol.* 27: 201-222.

Farenhorst, M., B. G. J. Knols, et al. (2010). "Synergy in Efficacy of Fungal Entomopathogens and Permethrin against West African Insecticide-Resistant *Anopheles gambiae* Mosquitoes." *PLoS ONE* 5(8): e12081.

Hoshino, T., T. Takano, et al. (1987). "Biosynthesis of violacein: origins of the hydrogen, nitrogen and oxygen atoms in the 2-pyrrolidone nucleus." *Agric. Biol. Chem.* 51: 2733-2741.

Hummelbrunner, L. A. and M. B. Isman (2001). "Acute, Sublethal, Antifeedant, and Synergistic Effects of Monoterpenoid Essential Oil Compounds on the Tobacco Cutworm, *Spodoptera litura* (Lep., Noctuidae)." *Journal of Agricultural and Food Chemistry* 49(2): 715-720.

Hungria, M., S. Astolfi-Filho, et al. (2005). "Genetic characterization of *Chromobacterium* isolates from black water environments in the Brazilian Amazon." *Lett. Appl. Microbiol.* 41: 17-23.

Krieg, A., A. M. Huger, et al. (1983). "*Bacillus thuringiensis* var. *tenebrionis*: Ein neuer, gegenuber Larven von Coleopteren wirksamer Pathotyp." *Z. Angew. Entomol.* 96: 500-508.

Kámpfer, P., H.-J. Busse, et al. (2009). "*Chromobacterium piscinae* sp. nov. and *Chromobacterium pseudoviolaceum* sp. nov., from environmental samples." *Int. J. Syst. Evol. Microbiol.* 59: 2486-2490.

Martin, P. A. W., D. Gundersen-Rindal, et al. (2007a). "*Chromobacterium substugae* sp. nov., a betaproteobacterium toxic to Colorado potato beetle and other insect pests." *Int. J. Syst. Evol. Microbiol.* 57: 993-999.

Martin, P. A., A. D. S. Shropshire, et al., (2007b). "*Chromobacterium substugae* sp. nov for control of insect pests" U.S. Pat. No. 7,244,607 B2.

Martin, P. A. W., Hirose, E., and Aldrich, J. R. 2007c. "Toxicity of *Chromobacterium substugae* to southern green stink bug (Heteroptera: Pentatomidae) and corn rootworm (Coleoptera: Chrysomelidae)". *J. Econ. Entomol.* 100: 680-684.

Martin, P. A. W. (2004). "A freeze-dried diet to test pathogens of Colorado potato beetle." *Biological Control* 29(1): 109-114.

McClean, K. H., M. K. Winson, et al. (1997). "Quorum sensing and *Chromobacterium violaceum*: exploitation of violacein production and inhibition for the detection of N-acyl homoserine lactones" *Microbiology* 143: 3703-3711.

Meunier, L., P. Carubel, et al. (1999). Insecticidal combinations including an insecticide from the family chloronicotinyl family and an insecticide having pyrazole, pyrrole, or phenylimidazole group. U. States. United States, Rhone-Poulene Agrochimie: 6.

Pederson, M. and H. S. Woldum. Synergistic Combination of Glutamate-and-Gaba-Gated Chloride Against Pesticide and at Least One Vitamin E, Niacin, or Derivatives Thereof, US 2009/0111579, published Apr. 30, 2009.

Puritch, G. and G. Salloum. Environmentally Safe Insecticide, U.S. Pat. No. 5,047,424, issued Sep. 10, 1991.

Shapiro-Ilan, D. I., T. E. Cottrell, et al. (2011). "Effects of combining microbial and chemical insecticides on mortality of the Pecan Weevil (Coleoptera: Curculionidae)." *J Econ Entomol* 104(1): 14-20

Ryan, K. S, and C. L. Drennan (2009). "Divergent pathways in the biosynthesis of bisindole natural products." *Chemistry&Biology* 16: 351-364.

Shapiro-Ilan, D. I., T. E. Cottrell, et al. (2011). "Effects of combining microbial and chemical insecticides on mortality of the Pecan Weevil (Coleoptera: Curculionidae)." *J Econ Entomol* 104(1): 14-20.

Thompson, G. D., R. Dutton, et al. (2000). "Spinosad—a case study: an example from a natural products discovery programme." *Pest Management Science* 56: 696-702.

Whitehead, A. G. (1998). *Plant nematode control.* Wallingford, UK, CAB International.

Wirth, M. C., J. A. Jiannino, et al. (2004). "Synergy between Toxins of *Bacillus thuringiensis* subsp. *israelensis* and *Bacillus sphaericus*." *Journal of Medical Entomology* 41: 935-941.

Young, C.-C., A. B. Arun, et al. (2008). "*Chromobacterium aquaticum* sp. nov., isolated from spring water samples." *Int. J. Syst. Evol. Microbiol.* 58: 877-880.

Zeck W. M. (1971) Ein Bonitierungsschema zur Feldauswertung von Wurzelgallenbefall. Pflanzenschutznachrichten Bayer 24, 1: 144-147.

What is claimed is:

1. An isolated compound having the structure:

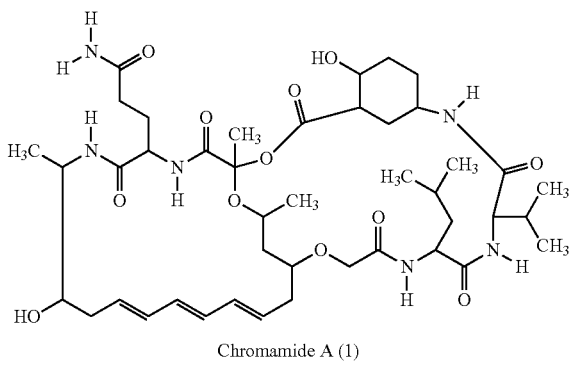 [SMILES: CC(C)CC1NC(=O)COC2C/C=C/C=C/C=C/CC(O)C(C)NC(=O)C(CCC(N)=O)NC(=O)C(C)(OC(=O)C3CC(CCC3O)NC(=O)C(C(C)C)NC1=O)OC(C)C2]

Chromamide A (1)

and which has insecticidal activity.

2. The isolated compound of claim 1, wherein the isolated compound is isolated from a *Chromobacterium* species.

3. The isolated compound of claim 2, wherein the *Chromobacterium* species is a *Chromobacterium subtsugae*.

4. The isolated compound of claim 3, wherein the *Chromobacterium subtsugae* is *Chromobacterium subtsugae* sp. nov. (NRRL B-30655).

5. A composition comprising the isolated compound of claim 1.

6. The composition of claim 5, further comprising at least one of a carrier, diluent, surfactant, or adjuvant.

7. The composition of claim 5, wherein the isolated compound is isolated from a *Chromobacterium* species.

8. The composition of claim 7, wherein the *Chromobacterium* species is a *Chromobacterium subtsugae*.

9. The composition of claim 8, wherein the *Chromobacterium subtsugae* is *Chromobacterium subtsugae* sp. nov. (NRRL B-30655).

10. A method for obtaining a compound from a *Chromobacterium* species comprising:
   (a) culturing a strain of the *Chromobacterium* species in a whole cell broth under conditions sufficient to produce said compound; and
   (b) isolating said compound produced in (a) from said whole cell broth, wherein the compound has a structure:

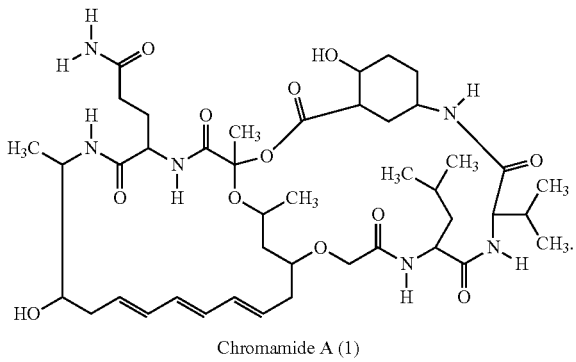 [SMILES: CC(C)CC1NC(=O)COC2C/C=C/C=C/C=C/CC(O)C(C)NC(=O)C(CCC(N)=O)NC(=O)C(C)(OC(=O)C3CC(CCC3O)NC(=O)C(C(C)C)NC1=O)OC(C)C2]

Chromamide A (1)

11. The method of claim 10, wherein the *Chromobacterium* species is a *Chromobacterium subtsugae*.

12. The method of claim 11, wherein the *Chromobacterium subtsugae* is *Chromobacterium subtsugae* sp. nov. (NRRL B-30655).

13. A method for modulating insect infestation in a plant comprising applying to the plant and/or seeds thereof and/or substrate used for growing said plant an amount of an isolated compound having the structure

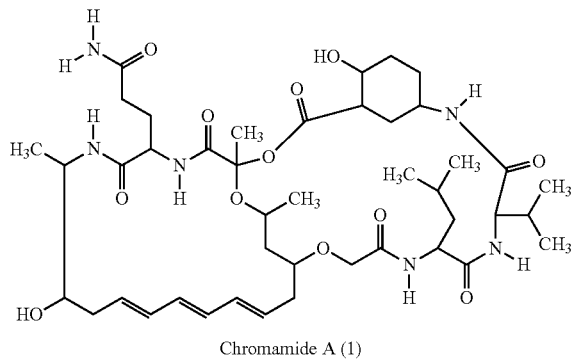 [SMILES: CC(C)CC1NC(=O)COC2C/C=C/C=C/C=C/CC(O)C(C)NC(=O)C(CCC(N)=O)NC(=O)C(C)(OC(=O)C3CC(CCC3O)NC(=O)C(C(C)C)NC1=O)OC(C)C2]

Chromamide A (1)

and which has insecticidal activity, effective to modulate said insect infestation.

14. The method of claim 13, wherein the isolated compound is isolated from a *Chromobacterium* species.

15. The method of claim 14, wherein the *Chromobacterium* species is a *Chromobacterium subtsugae*.

16. The method of claim 15, wherein the *Chromobacterium subtsugae* is *Chromobacterium subtsugae* sp. nov. (NRRL B-30655).

17. The method of claim 13, wherein the isolated compound is applied to the substrate.

18. The method of claim 17, wherein the substrate is soil.

19. The method of claim 13, wherein the isolated compound is applied to the plant.

20. The method of claim 13, wherein the isolated compound is applied to the seeds.

\* \* \* \* \*